US007605000B2

(12) United States Patent
Inouye et al.

(10) Patent No.: US 7,605,000 B2
(45) Date of Patent: Oct. 20, 2009

(54) COLD SHOCK INDUCIBLE EXPRESSION AND PRODUCTION OF HETEROLOGOUS POLYPEPTIDES

(75) Inventors: Masayori Inouye, New Brunswick, NJ (US); Sangita Phadtare, Highland Park, NJ (US); Bing Xia, Newton, MA (US); Guoliang Qing, Piscataway, NJ (US); Haiping Ke, Highland Park, NJ (US)

(73) Assignee: Takara Bio, Inc., Shiga (JP)

( * ) Notice: Subject to any disclaimer, the term of this patent is extended or adjusted under 35 U.S.C. 154(b) by 580 days.

(21) Appl. No.: 10/506,192

(22) PCT Filed: Feb. 25, 2003

(86) PCT No.: PCT/US03/05531

§ 371 (c)(1),
(2), (4) Date: Sep. 1, 2004

(87) PCT Pub. No.: WO03/074657

PCT Pub. Date: Sep. 12, 2003

(65) Prior Publication Data

US 2005/0272924 A1      Dec. 8, 2005

Related U.S. Application Data

(60) Provisional application No. 60/361,069, filed on Mar. 1, 2002, provisional application No. 60/402,921, filed on Aug. 14, 2002.

(51) Int. Cl.
*G01N 24/08* (2006.01)
*C12N 15/00* (2006.01)
*C12N 1/21* (2006.01)
*C12P 21/00* (2006.01)

(52) U.S. Cl. .................. 436/173; 435/320.1; 435/252.3; 435/252.33; 435/71.2

(58) Field of Classification Search ........................ None
See application file for complete search history.

(56) References Cited

U.S. PATENT DOCUMENTS

| | | | | |
|---|---|---|---|---|
| 5,395,614 | A * | 3/1995 | Knapp et al. | 424/272.1 |
| 6,294,711 | B1 | 9/2001 | Meulewaeter et al. | |
| 6,333,191 | B1 | 12/2001 | Inouye et al. | |
| 6,479,260 | B1 | 11/2002 | Takayama et al. | |
| 6,897,042 | B2 * | 5/2005 | Takayama et al. | 435/69.1 |
| 7,244,588 | B2 * | 7/2007 | Tomono et al. | 435/69.1 |

FOREIGN PATENT DOCUMENTS

| WO | WO 92/19718 | | 11/1992 |
|---|---|---|---|
| WO | WO 9927117 A1 * | | 6/1999 |

OTHER PUBLICATIONS

Yamanaka et al. Mutation analysis of the 5' untranslated region of the cold shock cspA mRNA of *Escherichia coli*. Journal of Bacteriology, vol. 181, No. 20, pp. 6284-6291, Oct. 1999.*

Tanabe et al. Identification of the promoter region of hte *Escherichia coli* major cold shock gene, cspA. Journal of Bacteriology, vol. 174, No. 12, pp. 3867-3873, Jun. 1992.*

Etchegaray et al. Translational enhancement by an element downstream of the initiation codon in *Escherichia coli*. The Journal of Biological Chemistry, vol. 274, No. 15, pp. 10079-10085, Apr. 1999.*

Vasina et al. Recombinant protein expression at low temperatures under the transcriptional control of the major *Escherichia coli* cold shock promoter cspA. Applied and Environmental Microbiology, vol. 62, No. 4, pp. 1444-1447, Apr. 1996.*

Vasina et al. Scale-up and optimization of the low-temperature inducible cspA promoter system. Biotechnol. Prog. vol. 14, pp. 714-721, 1998.*

Fang et al. Role of the cold-box region in the 5'-untranslated region of the cspA mRNA in its transient expression at low temperatures in Journal of Bacteriology, vol. 180, No. 1, pp. 90-95, Jan. 1998.*

Mackie. Stabilization of the 3'- one-thrid of *Escherichia coli* ribosomal protein S20 mRNA in mutants lacking polynucleotide phosphorylase. Journal of Bacteriology, vol. 171, No. 8, pp. 4112-4120, Aug. 1989.*

Phadtare and Severinov. Extended -10 motif is critical for activity of the cspA promoter but does not contribute to low-temperature transcription. Journal of Bacteriology, vol. 187, No. 18, pp. 6584-6589, Sep. 2005.*

Fang et al. Promoter-independent cold-shock induction of cspA and its derepression at 37 degrees C by mRNA stabilization. Molecular Microbiology, vol. 23, No. 2, pp. 355-364, 1997.*

Xia et al. The Cold Box stem-loop proximal to the 5'-end of the *Escherichia coli* cspA gene stabilizes its mRNA at low temperature. The Journal of Biological Chemistry, vol. 277, No. 8, pp. 6005-6011, Feb. 2002.*

Iost et al. mRNAs can be stabilized by DEAD-box proteins. Nature, vol. 372, No. 6502, pp. 193-196, Nov. 1994.*

Mitta, et al, "Deletion analysis of cspA of *Escherichia coli*: requirement of the AT-rich UP element for cspA transcription and the downstream box in the coding region for its cold shock induction". Molecular Microbiology. (1997). 26(2):321-335.

Mujacic, et al, "Cold-inducible cloning vectors for low-temperature protein expression in *Escherichia coli*: application to the production of a toxic and proteolytically sensitive fusion protein". Gene. (1999). 238: 325-332.

(Continued)

*Primary Examiner*—Christopher S. F. Low
*Assistant Examiner*—Jennifer Dunston
(74) *Attorney, Agent, or Firm*—Browdy and Neimark, PLLC

(57) ABSTRACT

The present invention relates to a DNA molecule or vector and a host cell containing this DNA molecule or vector which can be used to produce a heterologous polypeptide under conditions that elicit a cold shock response in the host cell. The DNA molecule and vector include a nucleotide sequence encoding a heterologous polypeptide and a promoter and 5'-UTR from a cold shock inducible gene which directs its expression. In addition, an AT-rich sequence that enhances translation under cold shock inducible conditions is either present in the coding sequence of the heterologous polypeptide or in an additional element inserted between the coding sequence and the cold shock inducible promoter and 5'-UTR.

22 Claims, 14 Drawing Sheets

OTHER PUBLICATIONS

Qing, et al, "Cold-shock induced high-yield protein production in *Escherichia coli*". Nature Biotechnology. (Jul. 2004). 22(7):877-882.

Yamanaka et al., Selective mRNA degradation by polynucleotide phosphorylase in cold shock adaptation in *Escherichia coli*, Journal of Bacteriology, 183(9)2808-2816 (May 2001).

Dammel et al., Suppression of a cold-sensitive mutation in 16S rRNA by overexpression of a novel ribosome-binding factor, RbfA, Genes & Development, 9:626-637 (1995).

Jones et al., Cold shock induces a major ribosomal-associated protein that unwinds double-stranded RNA in *Escherichia coli*, Proc. Natl. Acad. Sci. USA, 93:76-80 (1996).

* cited by examiner

ATGACTGGTGCANNNNNNNNNNNN-*lacZ* gene
initiation codon    random insertion sequence ATT TAT ATA TAT
β-galacosidase (U): 42,440

CGG TCT CTC CGC
β-galacosidase (U): 4410

```
                              SD
       Wt  CGCCGAAAGGCACACUUAAUUAUUAAAGGUAAUACACUAUGUCC
        1  CGCCGAAAGGCACAC[        ]AAGGUAAUACACUAUGUCC
        2  CGCCGAAAGGCACACUUAAUU[ ]UUAAAGGUAAUACACUAUGUCC
        3  CGCCGAAAGGCACACUUGAUUAUUAAAGGUAAUACACUAUGUCC
        4  CGCCGAAAGGCACACUUAACUAUUAAAGGUAAUACACUAUGUCC
        5  CGCCGAAAGGCACACUUGACUAUUAAAGGUAAUACACUAUGUCC
FIG.10A 6  CGCCGAAAGGCACACUUAAUUGUUAAAGGUAAUACACUAUGUCC
        7  CGCCGAAAGGCACACUUAACUGUUAAAGGUAAUACACUAUGUCC
        8  CGCCGAAAGGCACACUUGACUGUUAAAGGUAAUACACUAUGUCC
        9  CGCCGAAAGGCACAC[ ]AUUAUUAAAGGUAAUACACUAUGUCC
       10  CGCCGAAAGGCACACUUA[ ]AUUAAAGGUAAUACACUAUGUCC
       11  CGCCGAAAGGCACACUUAAUU[ ]AAGGUAAUACACUAUGUCC
       ─────────────────────────────────────────────────
       12  CGCCGAAAGGCACACUUAAUUAUUAAACCUAAUACACUAUGUCC
       13  CGCCGAAAGGCACAC[        ]AACCUAAUACACUAUGUCC
FIG.10B 14  CGCCGAAAGGCACACUUAAUUAUUA[ ]CCUAAUACACUAUGUCC
       15  CGCCGAAAGGCACACUUAAUUAUUA[   ]UAAUACACUAUGUCC
       16  CGCCGAAAGGCACACUUAAUUAUUA[       ]CACUAUGUCC
```

Insertion sequence for pColdI aaccgattaatcataaatatgaaaaataattgttgcatcacccgccaatgcgtggcttaatgcacatca
　　　　　　　　　　　cspA promoter acggtttgacgtacagaccattaaagcagtgtagtaaggcaagtcccttcaagagttatcgttgataccc
ctcgtagtgcacattcctttaacgcttcaaaatctgtaaagcacgccatatcgccgaaaggcacacttaa
ttattaaaggtaatacact
　　　　　　　　　　　cspA 5'UTR atgtccggtaaaatgactggtatcgtaaaatggttcaacgctgacaaaggcttcggcttcatcactcctga
cgatggctctaaagatgtgttcgtacacttctctgctatccagaacgatggttacaaatctctggacgaag
gtcagaaagtgtccttcaccatcgaaagcggcgctaaaggcccggcagctggtaacgtaaccagcctg
　　　　　　　　　　　cspA coding region <u>gtcgac</u><u>catcatcatcatcatcat</u> <u>atcgaaggtagg</u> <u>catatg</u>aagcttggtacc<u>ggatcc</u>
　　　　　　His tag　　　　　factor Xa site　 NdeI　　　　　　　BamHI tctctgcttaaaagcacagaatctaagatccctgccatttggcgggggatttttttatttgttttcaggaaataaat
aatcgatcgcgtaataaaatct
　　　　　　　　　　　cspA 3'UTR

FIG. 12A

Insertion sequence for pColdII aaccgattaatcataaatatgaaaaataattgttgcatcacccgccaatgcgtggcttaatgcacatca
                              cspA promoter acggtttgacgtacagaccattaaagcagtgtagtaaggcaagtcccttcaagagttatcgttgataccc
ctcgtagtgcacattcctttaacgcttcaaaatctgtaaagcacgccatatcgccgaaaggcacacttaa
ttattaaaggtaatacact
                   cspA 5'UTR <u>atgaatcacaaagtg</u> <u>catatgaagcttggtaccggatcc</u>
    DB         NdeI          BamHI tctctgcttaaaagcacagaatctaagatccctgccatttggcggggatttttttatttgttttcaggaaataaat
aatcgatcgcgtaataaaatct
               cspA 3'UTR

FIG. 12B

Insertion sequence for pColdIII aaccgattaatcataaatatgaaaaataattgttgcatcacccgccaatgcgtggcttaatgcacatca
                                cspA promoter acggtttgacgtacagaccattaaagcagtgtagtaaggcaagtcccttcaagagttatcgttgataccc
ctcgtagtgcacattcctttaacgcttcaaaatctgtaaagcacgccatatcgccgaaaggcacacttaa
ttattaaaggtaatacact
                          cspA 5'UTR <u>catatg</u>aagcttggtacc<u>ggatcc</u>
 NdeI             BamHI tctctgcttaaaagcacagaatctaagatccctgccatttggcggggatttttttatttgttttcaggaaataaat
aatcgatcgcgtaataaaatct
                      cspA 3'UTR

FIG. 12C

```
           UP          -35              -10      +1    Cold Box
cspI  TTTTCTTTAC AAAAGTAAT  CTGCTA TGGGTGGTTAATCATGC TTAAT GGTGTT--CT- GGTTTGTTACAAATTT ATCTGAAGCAGTCATTGT
cspG  GCCGGACGG. T....A...  AAT... T.ATC.CAA.T...... ..... -AGC.GC-G.C ....AA.G.C.GAC  G.AT.CAA...AG..TA
cspB  GC.GGA.GT. T....A..A.  .....T ATA..T.C..CT.....  ..... -.AT.GC-G.C ....AAGA.C.GAC ATAT.C.A...AG..TA
cspA  CA.AAA.ATC ....A....  TC...AT CACCC.CCA.TG.G.:GC ..... .CACA.CAA-C ....ACGT.C.GAC --.AT-TAA..CAG.GTA cspI  TATAA--TTTTATTATTTGTACCTCTTGACATTTCCTTGTTGGTTTT--TCTCTCT---GA----TA----TTT-T-TT-TT-CGGACCATTC
cspG  C.G..C.CA-..--.T.AGGCATT.TCC.....-C-T-...GAG......OCT..A-CAC..AGTAG...C.G-.A..AAA.C..TG.T
cspB  CTA...GCAG..C.C..-..C-.GG.G..ATTCAC.TA..CC.TC...GAG......CAATT.AGTACG.AGTCG...C.G..A.GCAAAC.AT..A
cspA  GTA.GGCAAG.CCCT.C-AAGAG.TA.CGTTGA.A.CCC.C.TAG.GCACA.TC.TTTAACGCTTCA.AATCTG.AAAGC-AC----.C.ATA..

Upstream                                      Downstream
      Sequence                  SD                    Box
cspI  TGCCCAAGGGCTA ATTTCTTCAA- AAGG TAAIAAT-TATGTCTAACAAA ATGACTGGTTTAGT GAAATGGTTTAAC
cspG  ...G..A...CC  ------AA..TG ...A .G....AA........T... ..............
cspB  ...G..A...TC  ------A.GT. ...A .-.GTAGA.....A..T... ..............
cspA  ...G..A...AC  C..AA.T.TTA ...A .A..CAC.....CGGT..  ........A.C. .........C...
```

FIG.13

NMR with purified protein

SEQUENCE LISTING

<160> NUMBER OF SEQ ID NOS: 50

<210> SEQ ID NO 1
<211> LENGTH: 539
<212> TYPE: DNA
<213> ORGANISM: Escherichia coli
<220> FEATURE:
<221> NAME/KEY: CDS
<222> LOCATION: (229)..(441)

<400> SEQUENCE: 1

```
aaccgattaa tcataaatat gaaaaataat tgttgcatca cccgccaatg cgtggcttaa      60
tgcacatcaa cggtttgacg tacagaccat taaagcagtg tagtaaggca agtcccttca     120
agagttatcg ttgataccccc tcgtagtgca cattccttta acgcttcaaa atctgtaaag    180
cacgccatat cgccgaaagg cacacttaat tattaaaggt aatacact atg tcc ggt     237
                                                     Met Ser Gly
                                                       1 aaa atg act ggt atc gta aaa tgg ttc aac gct gac aaa ggc ttc ggc       285
Lys Met Thr Gly Ile Val Lys Trp Phe Asn Ala Asp Lys Gly Phe Gly
  5                  10                  15 ttc atc act cct gac gat ggc tct aaa gat gtg ttc gta cac ttc tct       333
Phe Ile Thr Pro Asp Asp Gly Ser Lys Asp Val Phe Val His Phe Ser
 20                  25                  30                  35 gct atc cag aac gat ggt tac aaa tct ctg gac gaa ggt cag aaa gtg       381
Ala Ile Gln Asn Asp Gly Tyr Lys Ser Leu Asp Glu Gly Gln Lys Val
                 40                  45                  50 tcc ttc acc atc gaa agc ggc gct aaa ggc ccg gca gct ggt aac gta       429
```

```
Ser Phe Thr Ile Glu Ser Gly Ala Lys Gly Pro Ala Ala Gly Asn Val
            55                  60                  65 acc agc ctg taa tctctgctta aaagcacaga atctaagatc cctgccattt       481
Thr Ser Leu
        70 ggcggggatt ttttatttg ttttcaggaa ataataatc gatcgcgtaa taaaatct    539

<210> SEQ ID NO 2
<211> LENGTH: 70
<212> TYPE: PRT
<213> ORGANISM: Escherichia coli

<400> SEQUENCE: 2

Met Ser Gly Lys Met Thr Gly Ile Val Lys Trp Phe Asn Ala Asp Lys
1               5                   10                  15

Gly Phe Gly Phe Ile Thr Pro Asp Asp Gly Ser Lys Asp Val Phe Val
            20                  25                  30

His Phe Ser Ala Ile Gln Asn Asp Gly Tyr Lys Ser Leu Asp Glu Gly
        35                  40                  45

Gln Lys Val Ser Phe Thr Ile Glu Ser Gly Ala Lys Gly Pro Ala Ala
    50                  55                  60

Gly Asn Val Thr Ser Leu
65                  70

<210> SEQ ID NO 3
<211> LENGTH: 563
<212> TYPE: DNA
<213> ORGANISM: Escherichia coli
<220> FEATURE:
<221> NAME/KEY: CDS
<222> LOCATION: (215)..(430)

<400> SEQUENCE: 3
gctggatgtc taaataaac attgcttcat atgttcaact atgcgttaat gattgcgtcg    60
gtttgaagaa cagacgatat acgaagtagt ttactaaagc agttctcatt tcaggtgtta   120
ttcacttatt ccttctttga gtctctccaa ttaagtacga agtcgtttct gttatgcaaa   180
ccatttatgc cgaaaggctc aagttaagga atgt aga atg tca aat aaa atg act   235
                                       Arg Met Ser Asn Lys Met Thr
                                        1               5 ggt tta gta aaa tgg ttt aac gct gat aaa ggt ttc ggc ttt att tct   283
Gly Leu Val Lys Trp Phe Asn Ala Asp Lys Gly Phe Gly Phe Ile Ser
        10                  15                  20 cct gtt gat ggt agt aaa gat gtg ttt gtg cat ttt tct gcg att cag   331
Pro Val Asp Gly Ser Lys Asp Val Phe Val His Phe Ser Ala Ile Gln
    25                  30                  35 aat gat aat tat cga acc tta ttt gaa ggt caa aag gtt acc ttc tct   379
Asn Asp Asn Tyr Arg Thr Leu Phe Glu Gly Gln Lys Val Thr Phe Ser
40                  45                  50                  55 ata gag agt ggt gct aaa ggt cct gca gca gca aat gtc atc att act   427
Ile Glu Ser Gly Ala Lys Gly Pro Ala Ala Ala Asn Val Ile Ile Thr
                60                  65                  70 gat taaaattcat cgctcgtctg tatacgataa cgaagaaggc tgatgcctga        480
Asp gtagagatac ggacagagta gtgaatattg gatctcttta ataaaagta aggaggtcca   540 atacatgaaa caatggctag cat                                          563

<210> SEQ ID NO 4
```

```
<211> LENGTH: 72
<212> TYPE: PRT
<213> ORGANISM: Escherichia coli
<220> FEATURE:
<223> OTHER INFORMATION: Synthetic

<400> SEQUENCE: 4

Arg Met Ser Asn Lys Met Thr Gly Leu Val Lys Trp Phe Asn Ala Asp
1               5                   10                  15

Lys Gly Phe Gly Phe Ile Ser Pro Val Asp Gly Ser Lys Asp Val Phe
            20                  25                  30

Val His Phe Ser Ala Ile Gln Asn Asp Asn Tyr Arg Thr Leu Phe Glu
        35                  40                  45

Gly Gln Lys Val Thr Phe Ser Ile Glu Ser Gly Ala Lys Gly Pro Ala
    50                  55                  60

Ala Ala Asn Val Ile Ile Thr Asp
65                  70

<210> SEQ ID NO 5
<211> LENGTH: 520
<212> TYPE: DNA
<213> ORGANISM: Escherichia coli
<220> FEATURE:
<221> NAME/KEY: CDS
<222> LOCATION: (214)..(426)

<400> SEQUENCE: 5
cgccggacgg ctaaaataaa atttgcttaa tctcaattat catgcgttaa tagctgcgtc     60
ggtttgaaag acagacagca tacaaagtag tttactaaag cagttctcat tatcaggcat    120 tatcccttc ttttgagtct ctctcctgaa cactaagtag tttctgtatt aaagccctgt     180
ttgccgaaag gcccaaaatg aaggaagtaa aat atg tct aat aaa atg act ggt    234
                                   Met Ser Asn Lys Met Thr Gly
                                   1               5 tta gta aaa tgg ttt aac gca gat aaa ggt ttt ggc ttt atc act cct    282
Leu Val Lys Trp Phe Asn Ala Asp Lys Gly Phe Gly Phe Ile Thr Pro
        10                  15                  20 gat gat ggc agc aaa gac gtt ttc gtc cat ttc acc gcc atc cag agc    330
Asp Asp Gly Ser Lys Asp Val Phe Val His Phe Thr Ala Ile Gln Ser
 25                  30                  35 aat gaa ttc cgc acg ctg aac gaa aat cag aaa gtt gaa ttt tct att    378
Asn Glu Phe Arg Thr Leu Asn Glu Asn Gln Lys Val Glu Phe Ser Ile
40                  45                  50                  55 gag cag ggg caa cgt ggc ccc gcg gca gcg aac gtt gtt acg ctc taa    426
Glu Gln Gly Gln Arg Gly Pro Ala Ala Ala Asn Val Val Thr Leu
            60                  65                  70 ggttgccatt attactcaac atctccattt ccgctgtcca tgttgtcatg gttcacagta    486
ccgcacatcg gcattcgatg tgacggagcg aaac                                520

<210> SEQ ID NO 6
<211> LENGTH: 70
<212> TYPE: PRT
<213> ORGANISM: Escherichia coli
<220> FEATURE:
<223> OTHER INFORMATION: Synthetic

<400> SEQUENCE: 6

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
            20                  25                  30
```

His Phe Thr Ala Ile Gln Ser Asn Glu Phe Arg Thr Leu Asn Glu Asn
         35                  40                  45

Gln Lys Val Glu Phe Ser Ile Glu Gln Gly Gln Arg Gly Pro Ala Ala
     50                  55                  60

Ala Asn Val Val Thr Leu
65                  70

<210> SEQ ID NO 7
<211> LENGTH: 560
<212> TYPE: DNA
<213> ORGANISM: Escherichia coli
<220> FEATURE:
<221> NAME/KEY: CDS
<222> LOCATION: (202)..(414)

<400> SEQUENCE: 7
ttttctttac aaaagtaatc cttgctatgg gtggttaatc atgcgttaat ggtgttctgg      60
tttgttacaa atttatctga agcagtcatt gttataattt tattatttgt acctcttgag     120
atttccttgt tggttttct ctctgatatt tttttcgga ccattctgcc caagggctaa      180
tttcttcaaa aggtaataat t atg tct aac aaa atg act ggt tta gtg aaa      231
                         Met Ser Asn Lys Met Thr Gly Leu Val Lys
                          1               5                  10 tgg tgt aac cct gaa aaa ggt ttt ggt ttc atc acg ccg aaa gag ggc      279
Trp Cys Asn Pro Glu Lys Gly Phe Gly Phe Ile Thr Pro Lys Glu Gly
             15                  20                  25 agc aaa gat gtg ttt gtc cat ttc tca gca atg cag agc aac gat ttc      327
Ser Lys Asp Val Phe Val His Phe Ser Ala Met Gln Ser Asn Asp Phe
         30                  35                  40 aaa aca tta act gag aat cag gaa gtt gaa ttt ggt att gag aac gga      375
Lys Thr Leu Thr Glu Asn Gln Glu Val Glu Phe Gly Ile Glu Asn Gly
     45                  50                  55 cct aaa ggt cct gcc gct gtt cat gta gtg gcg ctt tga ggtagacaat      424
Pro Lys Gly Pro Ala Ala Val His Val Val Ala Leu
 60                  65                  70 attacaaacc atattcactt tagatgcccg tgttgtcatg gttcccagta tagaacatca     484
tcttttgatg tttctgacat gaatcctttc ggggcaaaat gtatcttttg taaatcaatg     544
atgattacat ttgata                                                     560

<210> SEQ ID NO 8
<211> LENGTH: 70
<212> TYPE: PRT
<213> ORGANISM: Escherichia coli
<220> FEATURE:
<223> OTHER INFORMATION: Synthetic

<400> SEQUENCE: 8

Met Ser Asn Lys Met Thr Gly Leu Val Lys Trp Cys Asn Pro Glu Lys
1               5                  10                  15

Gly Phe Gly Phe Ile Thr Pro Lys Glu Gly Ser Lys Asp Val Phe Val
             20                  25                  30

His Phe Ser Ala Met Gln Ser Asn Asp Phe Lys Thr Leu Thr Glu Asn
         35                  40                  45

Gln Glu Val Glu Phe Gly Ile Glu Asn Gly Pro Lys Gly Pro Ala Ala
     50                  55                  60

Val His Val Val Ala Leu
65                  70

```
<210> SEQ ID NO 9
<211> LENGTH: 21
<212> TYPE: DNA
<213> ORGANISM: Escherichia coli

<400> SEQUENCE: 9
atgaatcaca aagtgcatat g                                         21

<210> SEQ ID NO 10
<211> LENGTH: 26
<212> TYPE: DNA
<213> ORGANISM: Escherichia coli

<400> SEQUENCE: 10
attgtgagcg gataacaatt gatgtg                                    26

<210> SEQ ID NO 11
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(44)
<223> OTHER INFORMATION: n is a, c, g or t.

<400> SEQUENCE: 11
ggatctagag ggtattaata atgactggtg cannnnnnnn nnnn                44

<210> SEQ ID NO 12
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(24)
<223> OTHER INFORMATION: n is a, c, g or t.

<400> SEQUENCE: 12
atgactggtg cannnnnnnn nnnn                                      24

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(16)
<223> OTHER INFORMATION: n is a, c, g or t.

<400> SEQUENCE: 13
tgcannnnnn nnnnnnccaa                                           20

<210> SEQ ID NO 14
<211> LENGTH: 12
<212> TYPE: DNA
<213> ORGANISM: Artificial Sequence
<220> FEATURE:
<223> OTHER INFORMATION: Synthetic

<400> SEQUENCE: 14
atttatatat at                                                   12
```

```
<210> SEQ ID NO 15
<211> LENGTH: 12
<212> TYPE: DNA
<213> ORGANISM: Artificial Sequence
<220> FEATURE:
<223> OTHER INFORMATION: Synthetic

<400> SEQUENCE: 15
catttatata ta                                                          12

<210> SEQ ID NO 16
<211> LENGTH: 12
<212> TYPE: DNA
<213> ORGANISM: Artificial Sequence
<220> FEATURE:
<223> OTHER INFORMATION: Synthetic

<400> SEQUENCE: 16
tttatatata ta                                                          12

<210> SEQ ID NO 17
<211> LENGTH: 12
<212> TYPE: DNA
<213> ORGANISM: Artificial Sequence
<220> FEATURE:
<223> OTHER INFORMATION: Synthetic

<400> SEQUENCE: 17
acttttacaa ag                                                          12

<210> SEQ ID NO 18
<211> LENGTH: 12
<212> TYPE: DNA
<213> ORGANISM: Artificial Sequence
<220> FEATURE:
<223> OTHER INFORMATION: Synthetic

<400> SEQUENCE: 18
cacttttaca aa                                                          12

<210> SEQ ID NO 19
<211> LENGTH: 12
<212> TYPE: DNA
<213> ORGANISM: Artificial Sequence
<220> FEATURE:
<223> OTHER INFORMATION: Synthetic

<400> SEQUENCE: 19
cttttacaaa ga                                                          12

<210> SEQ ID NO 20
<211> LENGTH: 12
<212> TYPE: DNA
<213> ORGANISM: Artificial Sequence
<220> FEATURE:
<223> OTHER INFORMATION: Synthetic

<400> SEQUENCE: 20
acacatgaac ac                                                          12

<210> SEQ ID NO 21
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 21
cacacatgaa ca                                                         12

<210> SEQ ID NO 22
<211> LENGTH: 12
<212> TYPE: DNA
<213> ORGANISM: Artificial Sequence
<220> FEATURE:
<223> OTHER INFORMATION: Synthetic

<400> SEQUENCE: 22
cacatgaaca ca                                                         12

<210> SEQ ID NO 23
<211> LENGTH: 12
<212> TYPE: DNA
<213> ORGANISM: Artificial Sequence
<220> FEATURE:
<223> OTHER INFORMATION: Synthetic

<400> SEQUENCE: 23
catagttttc aa                                                         12

<210> SEQ ID NO 24
<211> LENGTH: 12
<212> TYPE: DNA
<213> ORGANISM: Artificial Sequence
<220> FEATURE:
<223> OTHER INFORMATION: Synthetic

<400> SEQUENCE: 24
ccatagtttt ca                                                         12

<210> SEQ ID NO 25
<211> LENGTH: 12
<212> TYPE: DNA
<213> ORGANISM: Artificial Sequence
<220> FEATURE:
<223> OTHER INFORMATION: Synthetic

<400> SEQUENCE: 25
atagttttca aa                                                         12

<210> SEQ ID NO 26
<211> LENGTH: 12
<212> TYPE: DNA
<213> ORGANISM: Artificial Sequence
<220> FEATURE:
<223> OTHER INFORMATION: Synthetic

<400> SEQUENCE: 26
cggtctctcc gc                                                         12

<210> SEQ ID NO 27
<211> LENGTH: 9
<212> TYPE: RNA
<213> ORGANISM: Artificial Sequence
<220> FEATURE:
<223> OTHER INFORMATION: Synthetic

<400> SEQUENCE: 27 uuaacuuua                                                              9

<210> SEQ ID NO 28
```

```
<211> LENGTH: 44
<212> TYPE: RNA
<213> ORGANISM: Artificial Sequence
<220> FEATURE:
<223> OTHER INFORMATION: Synthetic

<400> SEQUENCE: 28
cgccgaaagg cacacuuaau uauuaaaggu aauacacuau gucc              44

<210> SEQ ID NO 29
<211> LENGTH: 34
<212> TYPE: RNA
<213> ORGANISM: Artificial Sequence
<220> FEATURE:
<223> OTHER INFORMATION: Synthetic

<400> SEQUENCE: 29
cgccgaaagg cacacaaggu aauacacuau gucc                         34

<210> SEQ ID NO 30
<211> LENGTH: 43
<212> TYPE: RNA
<213> ORGANISM: Artificial Sequence
<220> FEATURE:
<223> OTHER INFORMATION: Synthetic

<400> SEQUENCE: 30
cgccgaaagg cacacuuaau uuuaaaggua auacacuaug ucc               43

<210> SEQ ID NO 31
<211> LENGTH: 44
<212> TYPE: RNA
<213> ORGANISM: Artificial Sequence
<220> FEATURE:
<223> OTHER INFORMATION: Synthetic

<400> SEQUENCE: 31
cgccgaaagg cacacuugau uauuaaaggu aauacacuau gucc              44

<210> SEQ ID NO 32
<211> LENGTH: 44
<212> TYPE: RNA
<213> ORGANISM: Artificial Sequence
<220> FEATURE:
<223> OTHER INFORMATION: Synthetic

<400> SEQUENCE: 32
cgccgaaagg cacacuuaac uauuaaaggu aauacacuau gucc              44

<210> SEQ ID NO 33
<211> LENGTH: 44
<212> TYPE: RNA
<213> ORGANISM: Artificial Sequence
<220> FEATURE:
<223> OTHER INFORMATION: Synthetic

<400> SEQUENCE: 33
cgccgaaagg cacacuugac uauuaaaggu aauacacuau gucc              44

<210> SEQ ID NO 34
<211> LENGTH: 44
<212> TYPE: RNA
<213> ORGANISM: Artificial Sequence
<220> FEATURE:
<223> OTHER INFORMATION: Synthetic

<400> SEQUENCE: 34
```

```
cgccgaaagg cacacuuaau uguuaaaggu aauacacuau gucc                    44
```

<210> SEQ ID NO 35
<211> LENGTH: 44
<212> TYPE: RNA
<213> ORGANISM: Artificial Sequence
<220> FEATURE:
<223> OTHER INFORMATION: Synthetic

<400> SEQUENCE: 35

```
cgccgaaagg cacacuuaac uguuaaaggu aauacacuau gucc                    44
```

<210> SEQ ID NO 36
<211> LENGTH: 44
<212> TYPE: RNA
<213> ORGANISM: Artificial Sequence
<220> FEATURE:
<223> OTHER INFORMATION: Synthetic

<400> SEQUENCE: 36

```
cgccgaaagg cacacuugac uguuaaaggu aauacacuau gucc                    44
```

<210> SEQ ID NO 37
<211> LENGTH: 41
<212> TYPE: RNA
<213> ORGANISM: Artificial Sequence
<220> FEATURE:
<223> OTHER INFORMATION: Synthetic

<400> SEQUENCE: 37

```
cgccgaaagg cacacauuau uaaagguaau acacuauguc c                       41
```

<210> SEQ ID NO 38
<211> LENGTH: 41
<212> TYPE: RNA
<213> ORGANISM: Artificial Sequence
<220> FEATURE:
<223> OTHER INFORMATION: Synthetic

<400> SEQUENCE: 38

```
cgccgaaagg cacacuuaau uaaagguaau acacuauguc c                       41
```

<210> SEQ ID NO 39
<211> LENGTH: 40
<212> TYPE: RNA
<213> ORGANISM: Artificial Sequence
<220> FEATURE:
<223> OTHER INFORMATION: Synthetic

<400> SEQUENCE: 39

```
cgccgaaagg cacacuuaau uaagguaaua cacuaugucc                         40
```

<210> SEQ ID NO 40
<211> LENGTH: 44
<212> TYPE: RNA
<213> ORGANISM: Artificial Sequence
<220> FEATURE:
<223> OTHER INFORMATION: Synthetic

<400> SEQUENCE: 40

```
cgccgaaagg cacacuuaau uauuaaaccu aauacacuau gucc                    44
```

<210> SEQ ID NO 41
<211> LENGTH: 34
<212> TYPE: RNA

<213> ORGANISM: Artificial Sequence
<220> FEATURE:
<223> OTHER INFORMATION: Synthetic

<400> SEQUENCE: 41
cgccgaaagg cacacaaccu aauacacuau gucc         34

<210> SEQ ID NO 42
<211> LENGTH: 42
<212> TYPE: RNA
<213> ORGANISM: Artificial Sequence
<220> FEATURE:
<223> OTHER INFORMATION: Synthetic

<400> SEQUENCE: 42
cgccgaaagg cacacuuaau auuaccuaa uacacuaugu cc         42

<210> SEQ ID NO 43
<211> LENGTH: 39
<212> TYPE: RNA
<213> ORGANISM: Artificial Sequence
<220> FEATURE:
<223> OTHER INFORMATION: Synthetic

<400> SEQUENCE: 43
cgccgaaagg cacacuuaau uauauaauac acuaugcc         39

<210> SEQ ID NO 44
<211> LENGTH: 35
<212> TYPE: RNA
<213> ORGANISM: Artificial Sequence
<220> FEATURE:
<223> OTHER INFORMATION: Synthetic

<400> SEQUENCE: 44
cgccgaaagg cacacuuaau uauuacacua ugucc         35

<210> SEQ ID NO 45
<211> LENGTH: 596
<212> TYPE: DNA
<213> ORGANISM: Artificial Sequence
<220> FEATURE:
<223> OTHER INFORMATION: Synthetic

<400> SEQUENCE: 45
aaccgattaa tcataaatat gaaaataat tgttgcatca cccgccaatg cgtggcttaa         60
tgcacatcaa cggtttgacg tacagaccat taaagcagtg tagtaaggca agtcccttca        120
agagttatcg ttgataccc tcgtagtgca cattccttta acgcttcaaa atctgtaaag        180
cacgccatat cgccgaaagg cacacttaat tattaaaggt aatacactat gtccggtaaa        240
atgactggta tcgtaaaatg gttcaacgct gacaaaggct tcggcttcat cactcctgac        300
gatggctcta aagatgtgtt cgtacacttc tctgctatcc agaacgatgg ttacaaatct        360
ctggacgaag gtcagaaagt gtccttcacc atcgaaagcg gcgctaaagg cccggcagct        420
ggtaacgtaa ccagcctggt cgaccatcat catcatcatc atatcgaagg taggcatatg        480
aagcttggta ccggatcctc tctgcttaaa agcacagaat ctaagatccc tgccatttgg        540
cggggatttt tttatttgtt ttcaggaaat aaataatcga tcgcgtaata aaatct          596

<210> SEQ ID NO 46
<211> LENGTH: 365
<212> TYPE: DNA
<213> ORGANISM: Artificial Sequence
<220> FEATURE:
<223> OTHER INFORMATION: Synthetic

<400> SEQUENCE: 46

| aaccgattaa tcataaatat gaaaaataat tgttgcatca cccgccaatg cgtggcttaa | 60 |
| tgcacatcaa cggtttgacg tacagaccat taaagcagtg tagtaaggca agtcccttca | 120 |
| agagttatcg ttgatacccc tcgtagtgca cattccttta acgcttcaaa atctgtaaag | 180 |
| cacgccatat cgccgaaagg cacacttaat tattaaaggt aatacactat gaatcacaaa | 240 |
| gtgcatatga agcttggtac cggatcctct ctgcttaaaa gcacagaatc taagatccct | 300 |
| gccatttggc ggggattttt ttatttgttt tcaggaaata ataatcgat cgcgtaataa | 360 |
| aatct | 365 |

<210> SEQ ID NO 47
<211> LENGTH: 350
<212> TYPE: DNA
<213> ORGANISM: Artificial Sequence
<220> FEATURE:
<223> OTHER INFORMATION: Synthetic

<400> SEQUENCE: 47

| aaccgattaa tcataaatat gaaaaataat tgttgcatca cccgccaatg cgtggcttaa | 60 |
| tgcacatcaa cggtttgacg tacagaccat taaagcagtg tagtaaggca agtcccttca | 120 |
| agagttatcg ttgatacccc tcgtagtgca cattccttta acgcttcaaa atctgtaaag | 180 |
| cacgccatat cgccgaaagg cacacttaat tattaaaggt aatacactca tatgaagctt | 240 |
| ggtaccggat cctctctgct taaaagcaca gaatctaaga tccctgccat ttggcgggga | 300 |
| ttttttattt tgttttcagg aaataaataa tcgatcgcgt aataaaatct | 350 |

<210> SEQ ID NO 48
<211> LENGTH: 162
<212> TYPE: RNA
<213> ORGANISM: Artificial Sequence
<220> FEATURE:
<223> OTHER INFORMATION: Synthetic

<400> SEQUENCE: 48

| acgguuugac guacagacca uuaaagcagu guaguaaggc aaguccuuc aagaguuauc | 60 |
| guugauaccc cucguagugc acauuccuuu aacgcuucaa aaucuguaaa gcacgccaua | 120 |
| ucgccgaaag gcacacuuaa uuauuaaagg uaauacacua ug | 162 |

<210> SEQ ID NO 49
<211> LENGTH: 25
<212> TYPE: RNA
<213> ORGANISM: Artificial Sequence
<220> FEATURE:
<223> OTHER INFORMATION: Synthetic

<400> SEQUENCE: 49

| ucccugccau uuggcgggga uuuuu | 25 |

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

```
-continued

Met Asn His Lys Val His Met
1               5
```

COLD SHOCK INDUCIBLE EXPRESSION AND PRODUCTION OF HETEROLOGOUS POLYPEPTIDES

BACKGROUND OF THE INVENTION

1. Field of the Invention

The present invention relates to a DNA molecule, vector, host and method for cold shock inducible expression and production of heterologous polypeptides.

2. Description of the Related Art

When *Escherichia coli* cells grown at 37° C. are transferred to a low temperature such as 15° C., a set of proteins called cold-shock proteins is transiently induced at a very high level during a growth lag period called the acclimation phase (Jones et al., 1987). These cold-shock specific proteins include: CspA, CspB, CspG, CspI, CsdA, RbfA, NusA, and PNP (for review see Phadtare et al., 1999, 2000 and 2002; Yamanaka et al., 1998). Among them, CspA has been identified as a major cold-shock protein consisting of 70 amino acid residues.

The CspA family of *E. coli* consists of nine homologous proteins, CspA to CspI, but among them only CspA, CspB, CspG and CspI are cold-shock inducible. Interestingly, the cspA gene is dispensable at both normal and low growth temperatures (Bae et al., 1997). None of the CspA homologues appears to be singularly responsible for cold-shock adaptation, as members of the CspA family functionally overlap each other during cold-acclimation of cells (Xia et al., 2001). Indeed, a ΔcspAΔcspBΔcspG triple deletion strain is still viable, while a ΔcspAΔcspBΔcspGΔcspE quadruple deletion strain is unable to form colonies at low temperature. Interestingly, any single gene from the nine CspA homologues except CspD has been shown to be capable of complementing the cold-sensitivity of the quadruple deletion strain (Xia et al., 2001). It has been shown that CspA is differentially regulated from CspB, CspG and CspI (Etchegaray et al., 1996 and Wang et al., 1999). High levels of CspA production are seen between 94° C. and 10° C., while CspB and CspG are produced only after temperature shifts to below 20° C., the maximum induction being at 15° C. CspI is induced between 10-15° C. It has also been shown that CspA, CspB and CspG are induced at low temperature under conditions that completely block protein synthesis (Etchegaray et al., 1999).

The cspA expression is regulated in a complex manner, that is at levels of transcription, mRNA stability and translation efficiency (for review see Phadtare et al., 2000 and Yamanaka et al., 1998). The cspA gene has an unusually long 5' untranslated region (5'-UTR) consisting of 159 bases. Deletion analysis of the cspA 5'-UTR showed that this region is responsible for its extreme instability at 37° C. (half-life less than 12 sec), and has positive effect on mRNA stabilization at low temperature (Jiang et al., 1996 and Mitta et al., 1997). The cspA mRNA is dramatically stabilized (half-life more than 20 min) immediately following cold shock. This stabilization is transient and is lost once cells are adapted to low temperature. This in turn regulates the expression of cspA.

The cold-shock induction of cspA is quite different from the heat-shock induction, as the cspA induction does not require a specific transcription factor. Interestingly, the cspA promoter is active at 37° C., but CspA is greatly reduced as the cspA mRNA is extremely unstable at this temperature. Thus, the 5'-UTR of the cspA mRNA plays a crucial role in its cold-shock inducibility. Recently, it has been shown that CspA is produced at 37° C. during early exponential growth phase and its mRNA becomes unstable by mid- to late-exponential growth phase (Yamanaka et al., 2001 and Brandi et al., 1999). The 5'-UTR region of the cspA mRNA contains a "Cold Box" sequence conserved among several cold-shock mRNAs. This region forms a stable stem-loop structure followed by an AU-rich sequence (Fang et al., 1998). The laboratory of the present inventors showed that this region is essential for the normal cspA mRNA induction after cold shock, as a deletion of the stem-loop significantly destabilizes the mRNA and reduces the cold shock-induced cspA mRNA amount by approximately 50%. The AU-rich track, however, slightly destabilizes the mRNA. The integrity of the stem is essential for the stabilizing function, while that of the loop sequence is less important (Xia et al., 2001).

Overexpression of a mutant cspA mRNA devoid of both the initiation codon (AUG) and the coding sequence results in a severe inhibition of growth at low temperature along with a derepression of the chromosomal cspA expression. Further, the overexpressed RNA is stably associated with the 30S and 70S ribosomes. Results from the laboratory of the present inventors demonstrated that the 5'-UTR by itself had a remarkable affinity to ribosomes at low temperature. Overproduction of the 5'-UTR at 15° C. results in delayed induction of the cold-shock response and in the prolonged synthesis of not only CspA, but also CspB and CspG (Fang et al., 1998 and Jiang et al., 1996). These effects are repressed by coproduction of the 5'-UTR together with CspA. The AT-rich sequence immediately upstream of the −35 region of the cspA promoter has been shown to function as an UP element to enhance cspA transcription. Deletion of the UP element resulted in diminished activity of the cspA promoter (Goldenberg et al., 1997 and Mitta et al., 1997). Another important factor that contributes towards higher promoter activity is the presence of a TGn motif immediately upstream of the −10 region (Kumar et al., 1993). It is reported that this motif together with the −10 region constitutes the extended −10 region and the −35 region is dispensable in the presence of this region.

Importantly, the expression of cspA is also regulated at the level of translation. The preferential synthesis of cold-shock proteins during the growth lag period (the acclimation phase) suggests that their mRNAs, unlike most other cellular (non-cold-shock) mRNAs, possess a mechanism to form the translation initiation complex at low temperature without the cold-shock ribosome factors, such as RbfA and CsdA. The recent data from the laboratory of the present inventors show that there are elements within the coding sequence of CspA that enhance its translation at low temperature. mRNAs for cold-shock proteins such as CspA, CspB, CspG, CspI, CsdA and RbfA have been proposed to have an element called the downstream box (DB) in the coding region which enhances translation initiation (Mitta et al., 1997). Originally, the DB sequence was proposed to be complementary to a region in the penultimate stem of 16S rRNA and is located a few bases downstream of the initiation codon. It has been debated how DB enhances translation initiation (Etchegaray et al., 1999 and O'Connor et al., 1999) and the originally proposed mechanism by facilitating the formation of translation preinitiation complex through binding to 16S rRNA may not be the precise mechanism.

The phenomenon termed as 'LACE' effect (low-temperature antibiotic effect of truncated cspA expression) was observed in *E. coli* (Jiang et al., 1996 and Xia et al., 2001). When a truncated cspA gene is overexpressed at low temperature, cell growth is completely blocked. This has been demonstrated to be caused due to the entrapment of almost all the cellular ribosomes by the truncated cspA mRNA. This truncated mRNA is still able to form the preinitiation complex with non-adapted ribosomes at low temperature. Unambiguous demonstration of ribosome entrapping by truncated cspA mRNA has been carried out by incorporating a terminator codon either at the second (pA01S), or the eleventh (pA10S) or the 31st (pA30S) codon in the cspA gene cloned in a pUC vector (Xia et al., 2001). At 37° C., cells carrying these plasmids are perfectly normal, while upon cold-shock cells stop to grow completely. They are unable to form colonies at 15° C. and with $^{35}$S-Met, no protein was labeled. When polysome profiles of these cells were analyzed, cells expressing only the initiation codon (pA01S) contained only monosomes without any polysome peaks. Cells with pA10S showed di- and monosomes and cells with pA30S showed tri-, di- and monosomes again without any large polysomal peaks. Furthermore, a major cellular mRNA (lpp) was shown to be excluded from polysomes by taken over being the truncated cspA mRNA. These results clearly demonstrate that the robust translatability of the cspA mRNA is determined at the step of initiation. In this study, the laboratory of the present inventors also showed that the upstream region within the 5'-UTR of the cspA mRNA plays an important role in the formation of the translation initiation complex leading to the LACE effect (Xia et al., 2001).

CspA and its homologues are proposed to be RNA chaperones by destabilizing secondary structures in mRNAs (Bae et al., 2000; Jiang et al., 1997 and Phadtare et al., 2001). Since the ΔcspAΔcspBΔcspGΔcspE quadruple deletion strain can not grow at low temperature while a single csp gene is able to complement the cold-sensitivity (Xia et al., 2001), the RNA chaperone function is considered to be crucial for efficient translation of cellular mRNAs at low temperatures by blocking stable secondary-structure formation, which is inhibitory to the mRNA translation (Phadtare et al., 2001).

Cold-inducible vectors containing the cspA promoter have been shown to be useful for expression of aggregation-prone proteins such as, preS2-S'-β-galactosidase and TolAI-β-lactamase (Mujacic et al., 1999; Vasina et al., 1997 and Vasina et al., 1996). U.S. Pat. No. 6,333,191 B1 discloses promoters of cspA and cspB and vectors carrying such promoters.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a DNA molecule and vector capable of expressing a heterologous polypeptide in a host cell under conditions that elicit a cold shock response in the host cell. The DNA molecule according to the present invention contains a nucleotide sequence encoding a heterologous polypeptide operably linked to a cold shock inducible gene promoter and 5'-untranslated region (5'-UTR) sequence which directs the expression and production of a heterologous polypeptide in a host cell under conditions that elicit a cold shock response. In addition, either the nucleotide sequence encoding the heterologous polypeptide has an AT rich sequence (naturally-occurring or created by, i.e., site-directed mutagenesis) at about the 4$^{th}$ to 7$^{th}$ codons downstream from the initiation codon or a translation enhancing element is inserted between the nucleotide sequence encoding the heterologous polypeptide and the cold shock inducible promoter and 5'-UTR sequence. This translation enhancing element contains an initiation codon and an AT rich sequence at about the 4$^{th}$ to 7$^{th}$ codons downstream from the initiation codon to form a translational in-frame fusion with the nucleotide sequence encoding the heterologous polypeptide.

The present invention also provides a host cell transformed with the DNA molecule or vector according to the present invention and a method of using such a host cell for producing a heterologous protein under cold shock inducible conditions, such as for whole cell or cell lysate NMR spectroscopy.

BRIEF DESCRIPTION OF THE DRAWINGS

(FIG. 2A) and 15° C. (FIG. 2B). In FIG. 2A, protein expression with (+) and without (−) IPTG in each case is shown. In FIG. 2B, expression of C. elegans proteins at 15° C. using cold shock vector is shown at 0, 12, and 24 h in each case.

FIGS. 10A and 10B show Epsilon-like sequences upstream of the SD sequence in the 5'-UTR cspA mRNA. FIG. 10A is a mutational analysis of the Epsilon-like sequence, where the wild-type sequence is shown as Wt (SEQ ID NO:28). The Epsilon sequence is shown in bold. FIG. 10B is a mutational analysis of the SD sequence and the distance between the Epsilon sequence and the AUG codon. The Epsilon-like sequences 1-16 are SEQ ID NOs:29-44, respectively.

FIGS. 12A-12C show nucleotide sequences, SEQ ID NO:45 (FIG. 12A), SEQ ID NO:46 (FIG. 12B), and SEQ ID NO:47 (FIG. 12C), which are inserted into the pUC19 vector cleaved with HindIII and EcoRI and filled in with Klenow.

FIG. 13 is a sequence alignment of the promoter, 5'-UTR, and the first 13 codon nucleotides of cspA (nucleotides 12-266 of SEQ ID NO:1), cspB (nucleotides 1-256 of SEQ ID NO:3), cspG (nucleotides 2-252 of SEQ ID NO:5) and cspI (SEQ ID NO:51). Nucleotides identical to cspI are shown as dots. To maximize the alignment, some gaps have been introduced and these are indicated by dashes. The transcription start sites are in bold letters and are marked as +1. The translation start codon ATGs are also in bold letters and are underlined. The most homologous sequences (UP element, −35 region, −10 region, cold box, upstream sequence, Shine-Dalgarno (SD) sequence, and downstream box) are boxed and indicated.

In FIG. 14B, lane 1: 50 µl total cell lysate loaded after cold shock 12 hrs; lane 2: 50 µl total cell lysate loaded after cold shock 24 hrs; lane 3: 50 µl total cell lysate loaded after cold shock 36 hrs; lane 4: 50 µl total cell lysate loaded after cold shock 48 hrs; lane 5: 2 µl of pellet (total 1 ml) loaded after 15,000 rpm, 30 min. centrifugation during second round of sonication; lane 6: 2 µl of pellet (total 1 ml) loaded after 45,000 rpm, 4 hr ultracentrifugation during second round of sonication; lane 7: 1 µl supernatant loaded after 45,000 rpm, 4 hr. ultra-centrifugation during second round of sonication; lane 8: 1 µl supernatant (sample for NMR) loaded after 45,000 rpm, 4 hr ultracentrifugation during the first round of sonication.

DETAILED DESCRIPTION OF THE INVENTION

Figure 1:
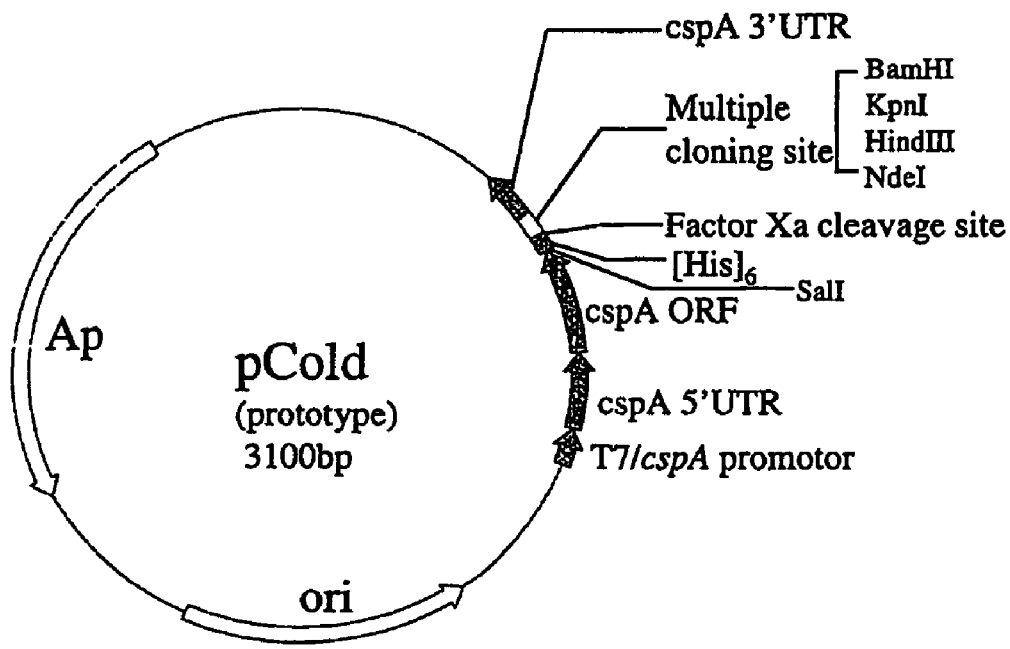
FIG. 1 shows a schematic representation of the structure of the prototype cold-shock vector pCold, where the (His)$_6$ feature is identified herein by SEQ ID NO:52.

Using Escherichia coli as a model system, the laboratory of the present inventors have found that there are a number of cold-shock proteins that are required for growth only at low temperature. Among these cold-shock proteins, CspA is the major cold-shock protein, and is induced upon cold shock at a level of more than $10^6$ molecules/cell ($10^{-4}$ M). The initiation of translation of the cspA mRNA is shown to be extraordinarily efficient at low temperatures and the cspA mRNA is found to possess the ability to suppress all other cellular mRNA translation. For example, when a nonsense codon is added immediately after the initiation codon of cspA, the mRNA from the truncated cspA gene in a pUC vector traps all the cellular ribosomes completely blocking other cellular protein synthesis upon cold shock and thereby completely inhibiting cell growth at low temperature. This phenomenon is termed as the "LACE effect". Therefore, using the remarkable translational advantage of the cspA mRNA together with its cold-shock-inducible mRNA stabilization and its highly efficient promoter, the present inventors designed a cold-shock inducible vector-host system in which all cellular ribosomes are dedicated only for the production of a cloned gene product at low temperature, thereby providing for extremely high expression of a gene product/protein of interest upon cold shock.

While cold-inducible vectors containing the cspA promoter have been shown to be useful for expression of aggregation-prone proteins such as preS2-S'-β-galactosidose and TolAI-β-lactamase (Mujacic et al., 1999; Vasina et al., 1996 and 1997), other elements are most critical for efficient translation at a low cold shock inducible temperature.

The present invention thus provides a DNA molecule capable of expressing a heterologous polypeptide under cold shock conditions, where the DNA molecule is preferably a self-replicating expression vector. The DNA molecule according to the present invention contains a nucleotide sequence encoding a heterologous polypeptide/protein of interest and a cold shock inducible promoter and 5'-untranslated region (5'-UTR) operably linked thereto to control and direct the expression and production of the heterologous polypeptide of interest in a host cell under conditions that elicit a cold shock response. In order to enhance translation efficiency, either the nucleotide sequence encoding the heterologous polypeptide has an AT rich sequence (naturally-occurring or created by, i.e., site-directed mutagenesis) at about the $4^{th}$ to $7^{th}$ codons downstream from the initiation codon or a translation enhancing element is inserted between polypeptide and the cold shock inducible promoter and 5'UTR sequence. This translation enhancing element contains an initiation codon and an AT rich sequence at about the $4^{th}$ or $7^{th}$ codons downstream from the initiation codon to form a translational in-frame fusion with the nucleotide sequence encoding the heterologous polypeptide.

The present inventors have discovered that the AT rich sequence enhances translation at the translation initiation step. It is proposed that the AT rich sequence, which does not have secondary structure downstream of the initiation codon, may facilitate ribosome entry, and thereby enhance the efficiency of translation initiation and subsequent elongation reaction. This in turn would increase the mRNA stability and the final polypeptide/protein production. Messenger RNA rich in A or A/T is unstructured and such an easily deformable mRNA is proposed to be efficiently accommodated by ribosomes, thus being favorable for translation initiation and/or early elongation.

The term "heterologous polypeptide" is intended to mean any polypeptide that is not naturally expressed from a cold shock inducible promoter in a naturally occurring host cell. Thus, while the "heterologous polypeptide" can be a polypeptide from the same source as the cold shock inducible promoter and 5'UTR, e.g., E. coli, as long as it is not naturally expressed from this promoter, preferably, this polypeptide is naturally expressed in a source different from the source of the cold shock inducible promoter and 5'-UTR, e.g., a non-E. coli source such as a human.

A DNA molecule is said to be "capable of expressing" a polypeptide, such as a heterologous polypeptide, if it contains nucleotide sequences which contain transcriptional and translational regulatory information, and such sequences are "operably linked" to nucleotide sequences which encode the polypeptide. An operable linkage is a linkage in which the regulatory DNA sequences and the DNA sequence sought to be expressed are connected in such a way as to permit gene expression. The regulatory regions needed for gene expression in general include a promoter region as well as the DNA sequences which, when transcribed into RNA, will signal the initiation of protein synthesis. Such regions will normally include those 5'-non-coding sequences involved with initiation of transcription and translation.

A promoter region would be operably linked to a DNA sequence if the promoter were capable of effecting transcription of that DNA sequence. As used herein, a "promoter sequence" is the sequence of the promoter which is found on the DNA and is transcribed by the RNA polymerase. Thus, to express the heterologous polypeptide, transcriptional and translational signals recognized by the host cell are necessary.

By the term "cold shock", it is meant that a host cell is subjected to a drop in incubation/growth temperature well below its normal physiological growth temperature, such as a temperature drop of at least about 13° C.

The term "AT-rich" as applied to a nucleotide sequence is defined as having an AT base content of at least 70%.

The cold shock inducible promoter and 5'UTR sequence is preferably any one of the cold shock inducible promoter and 5'-UTR sequences from an *E. coli* cspA, cspB, cspG or cspI gene. The nucleotide sequences of the promoter and 5'-UTR regions as well as the coding and 3'-UTR regions of the above *E. coli* cold shock proteins are presented as SEQ ID NO:1 (cspA) with SEQ ID NO:2 as the encoded CspA amino acid sequence, SEQ ID NO:3 (cspB) with SEQ ID NO:4 as the encoded CspB amino acid sequence, SEQ ID NO:5 (cspG) with SEQ ID NO:6 as the encoded CspG amino acid sequence, and SEQ ID NO:7 (cspI) with SEQ ID NO:8 as the encoded CspI amino acid sequence. The sequences are also available from the NCBI GenBank database under accession numbers AE000252 (CspB and CspI), AE000433 (CspA), and AE000201 (CspG). The promoter and 5'-UTR region sequences of cspA, cspB, cspG, and cspI correspond to nucleotides 22-441 of SEQ ID NO:1, nucleotides 11-214 of SEQ ID NO:3, nucleotides 1-2-913 of SEQ ID NO:5, and nucleotides 11-201 of SEQ ID NO:7, respectively, and are shown as an alignment in FIG. 13.

As will be appreciated by those of skill in the art, the cold shock inducible promoter and 5'-UTR for use in the DNA molecule of the present invention can be a fragment or a variant of the promoter and 5'-UTR sequences of any one of cspA, cspB, cspG or cspI as long as the ability to direct efficient expression and translation under cold shock inducible conditions is maintained. Fragments and variants in which certain sequences are deleted, substituted or inserted are intended to be encompassed by the present invention and guidance is provided in the Examples.

One preferred embodiment of the present invention is where there is an AT rich sequence already present in the $4^{th}$-$7^{th}$ codon of the nucleotide sequence encoding the heterologous polypeptide to serve as a translation enhancing element. This AT rich sequence can be either present in the naturally occurring nucleotide sequence encoding the heterologous polypeptide or can be introduced into the coding sequence by, i.e., site-directed mutagenesis. For instance, the AT content of the region from the codon 4 to codon 7 can be increased by replacing the third base of each codon to A or T if it is G or C. This can usually be done without altering the amino acid sequence of this region because of the degeneracy of codon usage.

Another preferred embodiment is where the cold shock inducible promoter and 5'-UTR sequence are preferably linked to the nucleotide sequence encoding the heterologous polypeptide by a translation enhancing element consisting of a nucleotide sequence of seven codons, where the first codon is an initiation codon and the $4^{th}$-$7^{th}$ codons form the AT rich sequence. An embodiment of such a translation enhancing element is the nucleotide sequence of nucleotides 1-18 of SEQ ID NO:9 as would be generated from cloning into the NdeI site of the pColdII vector described in Example 3.

Preferably, the DNA molecule according to the present invention also includes a 3'UTR sequence, such as a 3'UTR from any one of cspA, cspB, cspG, or cspI. A particularly preferred embodiment of a 3'UTR is the cspA 3'-UTR which includes nucleotides 442-539 of SEQ ID NO:1 or a fragment thereof.

In another embodiment, the DNA molecule of the present invention may optionally contain a lacI operator sequence, such as the nucleotide sequence of SEQ ID NO:10, immediately downstream from the transcription initiation site of the cold shock inducible promoter. Such a lacI operator may be used to circumvent problems if the heterologous polypeptide, even at a leaky low level of expression under non-induced conditions, is toxic to the growth of the host cell at its normal physiological growth temperature. In this way, the heterologous protein can only be produced under cold shock and in the presence of IPTG.

The present invention also provides a vector which contains the DNA molecule according to the present invention. Preferably, the vector is self-replicating and directs the expression of the heterologous polypeptide in a host cell under conditions that elicit a cold shock response. Preferred embodiments of the vector of the present invention are the pColdI, pColdII, and pColdIII vectors described in Example 3. These three vectors all have the same pUC19 backbone (cleaved at HindIII and EcoRI and then filled in with Klenow) but the insert sequences are different. FIGS. 12A-12C show the insert sequences for pColdI, II, and III, respectively.

Another aspect of the present invention provides for a prokaryotic host cell transformed with the DNA molecule or vector according to the present invention. Preferably, the host cell is *Escherichia coli*. As discussed in Example 4 herein, it is preferred that the host cell be a polynucleotide phosphorylase (pnpase) mutant lacking polynucleotide phosphorylase activity (pnp⁻) or a rbfA mutant lacking the 15 kDa RbfA protein that associates with free 30s ribosomal subunit but not the 70s ribosomal subunit (rbfA⁻). Another preferred embodiment of the host cell of the present invention is a host cell that is both pnp⁻ and rbfA⁻. Further embodiments include a host cell that is a csdA RNA helicase mutant lacking CsdA RNA helicase activity (csdA⁻) and a host cell that is co-transformed with a vector which overexpresses CsdA RNA helicase in the host cell. These csdA⁻ or CsdA overexpressing host cells are preferably also pnp⁻ and/or rbfA⁻.

A further aspect of the present invention is directed to a method for producing a heterologous polypeptide, including but not limited to, a medically important protein such as human proteins useful as therapeutics or as targets, proteins susceptible to heat denaturation, labeled proteins and proteins for use in NMR studies. The method involves culturing the host cell of the present invention containing the DNA molecule or vector of the present invention in a nutrient medium at the normal physiological growth temperature of the host cell and then subjecting the cultured host cell to cold shock by lowering the incubation temperature to a temperature at least 13° C. below the normal physiological growth temperature of the host cell to induce production of the heterologous polypeptide. The cold shocked host cell is kept at the lowered cold shock temperature to produce the heterologous polypeptide during the production phase. The produced heterologous polypeptide is subsequently recovered. In another embodiment, the incubation temperature is lowered to at least 20° C. below the normal physiological growth temperature of the host cell.

The advantages of the method of present invention are as follows:

1. Since protein induction is carried out by temperature downshift, no chemical inducers such as IPTG are required.
2. Upon cold shock, cells are converted into a protein-synthesizing machinery dedicated to a single protein of interest. The synthesis of all the other proteins is virtually blocked in the cells, as all the cellular ribosomes are entrapped with the mRNA for the protein cloned in the vector.
3. Therefore, by exchanging the medium after cold shock (for example from a $^{12}$C-glucose/$^{14}$NH$_4$Cl-base medium to a $^{13}$C-glucose/$^{15}$NH$_4$Cl-base medium), only the protein of interest can be labeled with isotopes, eliminating the purification process for the $^{13}$C, $^{15}$N-isotope labeled sample.
4. If a protein of a molecular weight 20 kDa is produced (at a level of 60% of the total cellular protein and note that only this protein is newly synthesized upon cold shock), the total yield of the protein per liter is approximately 120 mg. Provided that 80% of this protein is produced in a soluble form, with a cell suspension in 4 ml buffer or a cell lysate prepared from the suspension (sonicated and subsequently centrifuged to remove cell debris and the membrane fraction), one can obtain 25 mg/ml or 1.25 mM solution of the protein of interest, which can be directly used for NMR spectroscopy.
5. As NMR spectroscopy can be done with less than 1 ml, the culture size now can be reduced to 250 ml, which cuts the usage of expensive $^{13}$C-glucose and $^{15}$N—NH$_4$Cl [or ($^{15}$NH$_4$)$_2$SO$_4$] to a quarter. Furthermore, as the cells are unable to grow upon cold shock under the proposed conditions, the overall carbon utilization should be much less than the growing cells. Therefore, the concentration of glucose in the medium could be less than the concentration usually used for $^{13}$C-glucose (0.2%). This further saves the consumption of the expensive $^{13}$C-glucose.
6. Some proteins are highly susceptible to heat denaturation. In particular, expression of proteins in *E. coli* from those organisms usually living at lower temperature environments (such as *Caenorhabditis elegans*) is problematic to express at higher temperature. The proposed cold-shock-vector-host system circumvents this problem.
7. Although expression of some proteins may be higher with the T7 vector system, other protein expression may be achieved only with the proposed cold-shock-vector-system not only because of protein folding problems, but also because of transcriptional and translational regulation. This may become more and more evident as an extremely large number of genes from humans to bacteria become available.
8. As more and more medically important human proteins are identified, it is important to express these proteins in a soluble form and in a large amount. The cold-shock vector system according to the present invention serves as an alternative or complementary system for the conventional T7 expression system.

As will be appreciated by those of skill in the art, the method for producing a heterologous polypeptide according to the present invention can be used to incorporate a detectably labeled compound, such as a compound labeled with $^{13}$C or $^{15}$N, which are isotopes normally found in not more than negligible amounts in the host cell. When a detectably labeled compound is desired to be incorporated into the heterologous polypeptide produced by the present method, such as for NMR spectroscopy analysis, the nutrient medium is exchanged/replaced with a medium containing a compound for detectably labeling the heterologous polypeptide. The detectably labeled compound is preferably $^{15}$NH$_4$Cl, ($^{15}$NH$_4$)$_2$SO$_4$, $^{13}$C-glucose, a single amino acid residue labeled with $^{15}$N, a single amino acid residue labeled with $^{13}$C, or a single amino acid residue labeled with both $^{15}$N and $^{13}$C. Whereas $^{15}$NH$_4$Cl, ($^{15}$NH$_4$)$_2$SO$_4$, and $^{13}$C-glucose provide non-selective labeling throughout the produced heterologous polypeptide, a single amino acid residue, i.e., Glu, labeled with $^{15}$N and/or $^{13}$C provides selective labeling at residue positions in the heterologous polypeptide corresponding to the particular single amino acid residue.

Example 5 presented hereinbelow demonstrates the production of a heterologous polypeptide (ATP-binding domain of EnvZ) suitable for NMR spectroscopy of cell lysate supernatant without protein purification. The *E. coli* B strain BL21 used as the host cell in Example 5 is not a mutant lacking any of the major cold shock proteins, e.g., CspA. However, in the event that less background noise in NMR spectroscopy, resulting from the presence of labeled major cold shock proteins, is desired, a mutant host cell lacking one or more of the major cold shock proteins, preferably lacking CspA or a combination of CspA and another cold shock protein such as for example in the quadruple mutant ΔcspA ΔcspBΔcspGΔcspE, can be used instead.

The present invention further provides a method for obtaining a NMR spectrum of a heterologous polypeptide. This method involves culturing in a nutrient medium a prokaryotic host cell transformed with a nucleic acid comprising a nucleotide sequence encoding a heterologous polypeptide and capable of expressing and producing the heterologous polypeptide in response to cold shock. This is followed by subjecting the cultured host cell to cold shock by lowering the incubation temperature to a temperature below the normal physiological growth temperature of the host cell to induce the production of the heterologous polypeptide. After cold shock, the nutrient medium is exchanged/replaced with a medium containing a compound for detectably labeling the heterologous polypeptide. The cold shocked host cell is incubated at the lowered incubation temperature to produce the heterologous polypeptide detectably labeled with the compound, and then isolated. NMR spectroscopy can be conducted on either the isolated cold shocked host cell (whole cell NMR spectroscopy) or on the supernatant from cell lysate of the isolated cold shocked host cell to obtain a NMR spectrum of the heterologous polypeptide.

Having now generally described the invention, the same will be more readily understood through reference to the following examples which are provided by way of illustration and are not intended to be limiting of the present invention.

EXAMPLE 1

Construction of Prototype Vectors

A pUC19 vector (New England BioLabs, Beverly, Mass.) without the NdeI site was created by digesting the original plasmid with NdeI followed by Klenow filling and ligation was created. The PCR product including the T7/cspA promoter, the 5'-UTR region of CspA, and its coding region was cloned in the pUC19ΔNdeI plasmid in the EcoRI and HindIII sites. These two restriction sites were then deleted by Klenow filling. By site-directed mutagenesis, SalI and BamHI sites were created immediately after the cspA stop codon. A second DNA fragment containing a six His-tag, factor-Xa site for protease cleavage, and multiple cloning sites including NdeI, HindIII, and KpnI and the 3' region of cspA was synthesized and was cloned in this vector. The map of the prototype plasmid vector is shown in FIG. 1.

Cloning and Expression of the Proteins from *Caenorhabditis elegans*

Figures 2A, 2B:
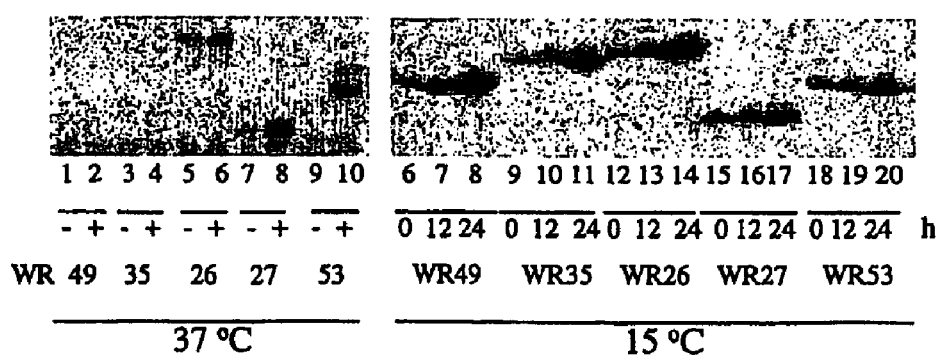
FIGS. 2A and 2B are gels showing expression of C. elegans proteins at 37° C.

Some proteins are highly susceptible to heat denaturation. In particular, expression of proteins in *E. coli* from those organisms usually living at lower temperature environments (such as *C. elegans*) is problematic to express at higher temperature. Five *C. elegans* proteins were chosen and were provided by Dr. G. Montelione (designated as WR49, WR35, WR26, WR27, and WR53, Genebank accession numbers: AV185320, AV183398, C50788, D71923 and C48848, respectively) that were cloned in pET vector and could not be expressed well at 37° C. (FIG. 2A). The inserts containing genes encoding these proteins were sub-cloned in the cold shock vector described in FIG. 1. The cells were grown at 37° C. to the OD600 nm of 0.5 and then they were transferred to 15° C. and were induced with 1 mM IPTG (isopropyl b-D thiogalactopyranoside in order to induce T7 promoter) and samples were removed at 0, 12 and 24 h and the protein expression was analyzed by SDS-PAGE. FIG. 2A shows the expression level of all these proteins at 37° C. using pET vectors after 3 h induction with 1 mM IPTG and FIG. 2B shows their expression at 15° C. using the respective cold-shock vectors. The proteins WR49 and WR35 could not be expressed at all at 37° C. using the pET expression vectors (lanes 2 and 4 in FIG. 2A, respectively). The protein WR26 was very poorly expressed (lane 6, FIG. 2A). All of these three proteins were greatly expressed at 15° C. using cold shock vectors. The expression of proteins WR27 and WR53 was also significantly higher using the cold shock vectors. Cold-shock vectors were also successfully used for expression of human proteins that otherwise could not be expressed well with conventional vectors.

Time Profile of Production of *C. elegans* Proteins.

Figure 3:
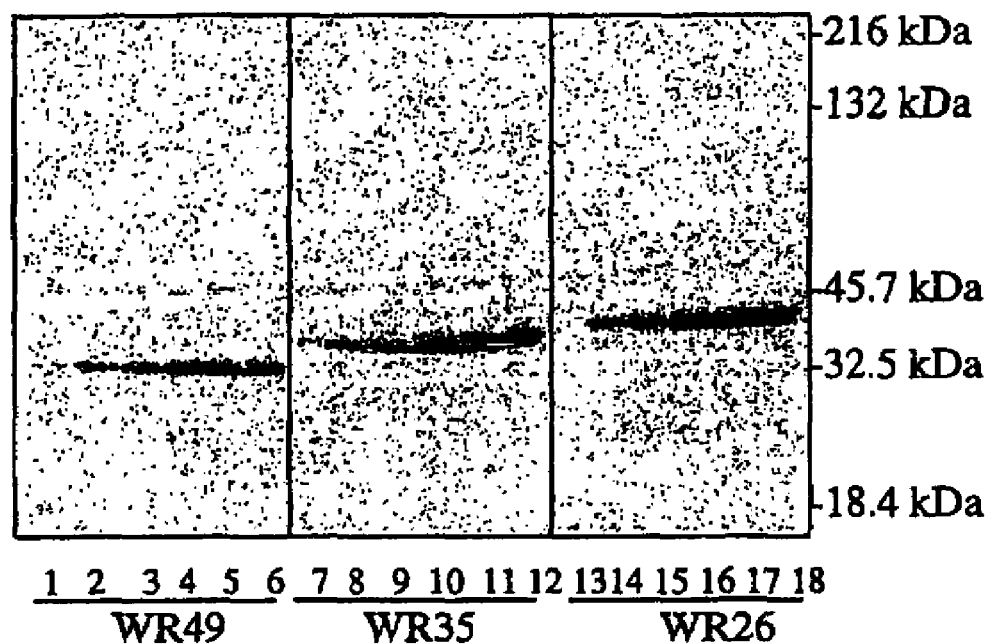
FIG. 3 are gels showing three time profile of production of C. elegans proteins with cold shock vector. 0, 24, 48, 72, 96 and 120 h expression of WR49, WR35, and WR126 at 15° C. is shown. The total cell lysates were analyzed. The gels were stained with Coomassie Blue dye.

Next, the time profile of production of proteins using the cold shock vectors was examined. WR49, WR35 and WR26 proteins that either could not be expressed at all or expressed very poorly at 37° C. using the conventional T7 vectors were chosen (FIG. 2A). The cells containing respective plasmids were grown at 37° C. to the OD600 nm of 0.5 and then they were transferred to 15° C. and were induced with 1 mM IPTG and samples were removed at 24 h intervals from 0-120 h and the protein expression was analyzed by SDS-PAGE. FIG. 3 shows the expression level of these proteins. Maximum expression of each protein was seen within 3-4 days and was maintained stably afterwards. Secondly, the expression of all other cellular proteins was significantly inhibited, resulting in production of protein of interest that is around 85% pure.

Figures 4A, 4B:
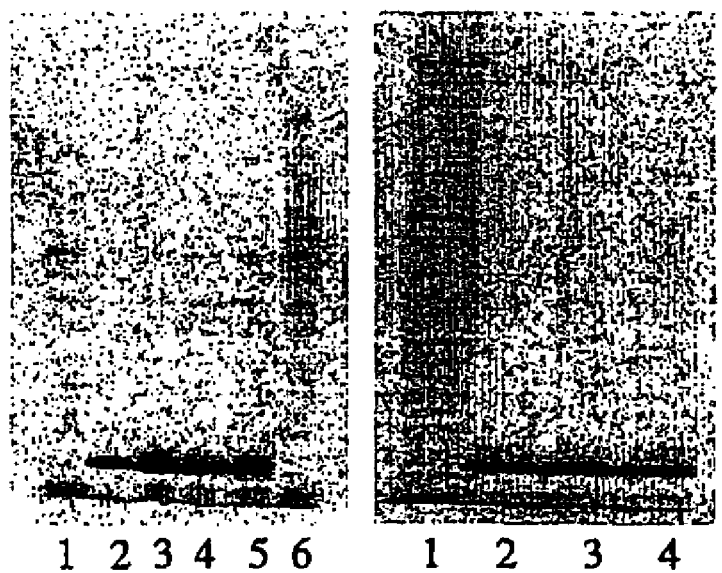
FIGS. 4A and 4B are SDS-PAGE analyses of the expression of γ-interferon using the cold shock vector. Coomassie staining of SDS-PAGE is shown in FIG. 4A Lane 1: before IPTG at 15° C.; Lanes 9-5: 24, 48, 72 and 96 h expression, respectively, at 15° C.; lane 6: expression at 37° C. SDS-PAGE analysis of pulse-labeled cells is shown in FIG. 4B. Lane 1: expression at 37° C.; lanes 2-4: 1 h, 3 h and 5 h expression, respectively, at 15° C.

Expression of Proteins Using Cold Shock Vectors Containing Only the cspA Promoter A specific aim of the present inventors is to synthesize a protein of interest at a translation efficiency of 90-95% in a cell, with a protein yield of higher than 60-70% of the total cellular proteins, where cell lysate or direct cell suspensions may be directly used for NMR spectroscopy. The fusion protein poses a problem in this aspect as separation and purification of the protein of interest from CspA is required before NMR spectroscopy. Hence, the laboratory of the present inventors have also constructed the cold-shock vectors with cspA promoter without the cspA coding region. The vector also contains a lac operator upstream of the cspA 5'UTR, thus the gene of interest can be induced by IPTG. The protein γ-interferon that is important from a medical perspective was chosen. The gene encoding γ-interferon was cloned in this vector and its production at 15° C. was checked as for the *C. elegans* proteins described above. FIG. 4A shows expression of γ-interferon protein at 37° C. and 15° C. Consistent with the fact that the cspA 5'UTR is responsible for the instability of cspA mRNA and therefore its lack of expression at 37° C., no γ-interferon expression was observed at this temperature (lane 6). On the other hand, it was well expressed at 15° C. (lanes 2-5). However, other cellular proteins are likely to be present as a result of carry over from the growth at 37° C. In order to check this possibility the cells were pulse-labeled at 15° C. The cells were grown in the labeling medium to the exponential phase and shifted to 15° C. One ml portions of the culture were labeled with 5 ml of $^{35}$S-methionine as described previously (Xia et al., 2001). Cells were chased by the addition of non-radioactive methionine. Cells were washed with 20 mM sodium phosphate buffer (pH 7.0) and were resuspended in 100 ml SDS sample buffer. Samples were analyzed by SDS-PAGE. γ-Interferon was now found to comprise more than 90% of the cellular labeled proteins (FIG. 4B, lane 2). This suggests that γ-interferon can be almost exclusively produced at 15° C. with the cold-shock vector. This method thus will be extremely useful in labeling the proteins specifically with isotopes such as $^{13}$C and $^{15}$N allowing a whole cell NMR spectroscopy without protein purification.

Identification of mRNA Downstream cis-Elements Favoring the Initiation of Protein Synthesis In order to further improve the present cold-shock vector system, the laboratory of the present inventors explored the mRNA cis-elements downstream of the initiation codon favoring the initiation of protein synthesis by constructing a molecular repertoire through a lacZ expression system. The sequence used was as follows: 5'-GGATCTAGAGGGTAT-TAATA<u>ATG</u>ACTGG TGCA<u>NNNNNNNNNNNN</u>-lacZ- termination signal-3' (SEQ ID NO:11). The initiation codon and the random insertion sequence are underlined. This sequence was cloned in IPTG-inducible pINIII vector (Inouye, 1983) and the plasmid was transformed in CL83 cells. 130 clones were randomly selected and sequenced.

Figure 5:
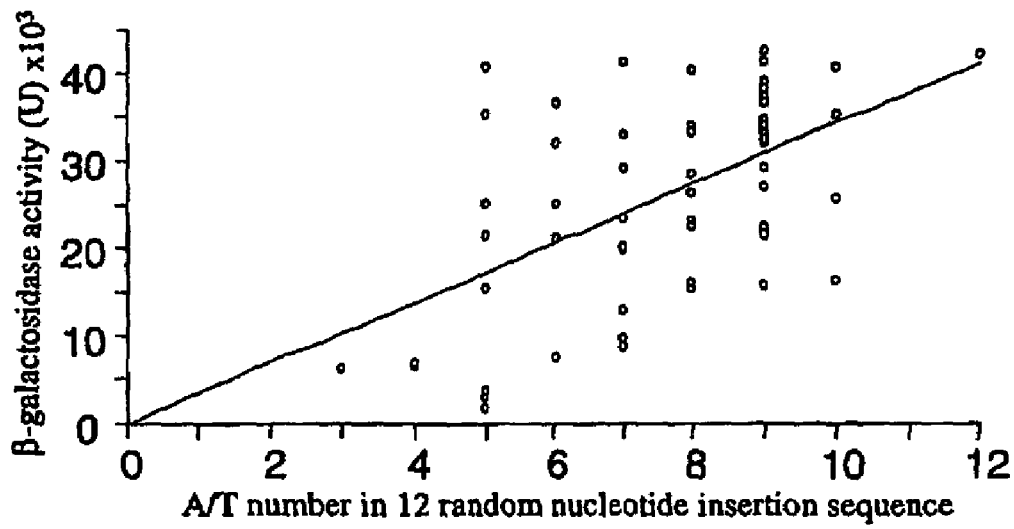
FIG. 5 is a graph showing correlation between the A/T contents of the N$^{12}$-downstream sequences and β-galactosidase activities. For each of the 57 randomly selected clones, the number of A plus T was counted and plotted against the corresponding β-galactosidase activity (SEQ ID NO:13).

Out of 130 clones, 57 were chosen for measurement of β-galactosidase activity according to the method of Miller (Miller, 1992). Most interestingly, the range of β-galactosidase activity is from 1,500 to 43,000 units, indicating that the coding region for codon 4 to codon 7 plays an important role in gene expression. Although there is not any one particular consensus sequence being responsible for higher enzyme activities (data not shown), the ratio of (A+T)/(A+T+G+C) was nearly 70% in the clones showing high β-galactosidase activities (FIG. 5). It was also apparent that in the clones showing higher lacZ expression, the most frequently used codons were the ones encoding amino acids such as Tyr, Thr, Leu and Ile. Four clones with high β-galactosidase activity were chosen and frame-shift were introduced mutations in each of them. As seen from Table 1, none of the mutations had any significant effect on the lace expression, except of the two mutations that resulted in introduction of stop codons (underlined in the Table).

TABLE 1

The Effects of Frame-Shift Mutations on β-Galactosidase Activity

| Insertion sequence: | TGCANNNNNNNNNNNNNCCAA | (SEQ ID NO:13) | β-galactosidase (U) |
|---|---|---|---|
| Clone 1: | | | |
| Original sequence | ATT TAT ATA TAT | (SEQ ID NO:14) | 42440 |
| Frameshift mutation | CAT TTA TAT ATA | (SEQ ID NO:15) | 41823 |
| Frameshift mutation | TTT ATA TAT ATA | (SEQ ID NO:16) | 42220 |
| Clone 2: | | | |
| Original sequence | ACT TTT ACA AAG | (SEQ ID NO:17) | 42150 |
| Frameshift mutation | CAC TTT TAC AAA | (SEQ ID NO:18) | 41823 |
| Frameshift mutation | CTT TTA CAA AGA | (SEQ ID NO:19) | 43824 |
| Clone 3: | | | |
| Original sequence | ACA CAT GAA CAC | (SEQ ID NO:20) | 37228 |
| Frameshift mutation | CAC ACA <u>TGA</u> ACA | (SEQ ID NO:21) | 519 |
| Frameshift mutation | CAC ATG AAC ACA | (SEQ ID NO:22) | 35495 |
| Clone 4: | | | |
| Original sequence | CAT AGT TTT CAA | (SEQ ID NO:23) | 35804 |
| Frameshift mutation | CCA <u>TAG</u> TTT TCA | (SEQ ID NO:24) | 759 |
| Frameshift mutation | ATA GTT TTC AAA | (SEQ ID NO:25) | 35100 |

Thus, specific codon usage did not have any obvious effect on the lacZ expression. This supports the notion that the high AT content is important for higher expression. Therefore the translation enhancing effect of the downstream box appears to be due to its higher AT (AU) content rather than its complementary sequence to the 16S RNA. The A/T-rich sequences downstream of the start codon may enhance the protein translation in E. coli, because the less stable secondary structure of A/T-rich sequences may result in the increased number of ribosomes initiating.

The Increased β-Galactosidase Activity is Due to Increased Protein Expression

Figure 6:
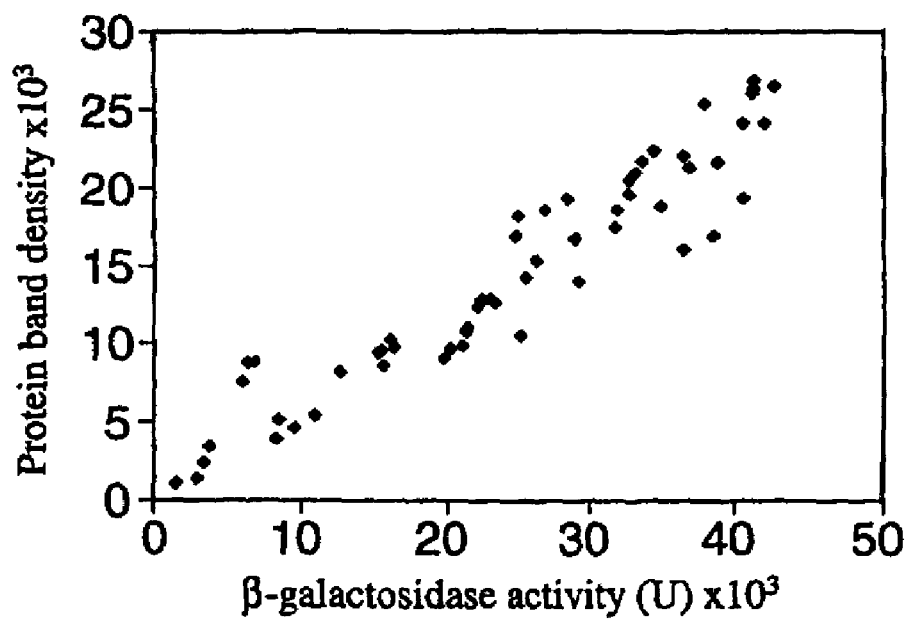
FIG. 6 shows a graph of the relationship between protein levels and β-galactosidase activities of the selected clones. The cells containing respective plasmids were grown at 37° C. to the OD$_{600}$ nm of 0.5 and were induced with 1 mM IPTG. The protein expression was analyzed by SDS-PAGE and band intensities were measured by densitometric analysis.

Fifty-seven of the above clones were further analyzed with respect to their protein profile and β-galactosidase activities. The cells containing respective plasmids were grown at 37° C. to the OD600 nm of 0.5 and were induced with 1-M IPTG. The protein expression was analyzed by SDS-PAGE and the protein-band densities were measured by densitometric analysis. The β-galactosidase activities were carried out as described before. As seen from FIG. 6, the β-galactosidase activities well correspond to the respective protein levels. The present inventors conclude that the higher β-galactosidase activity is due to higher specific activity of the protein itself.

Figure 7:
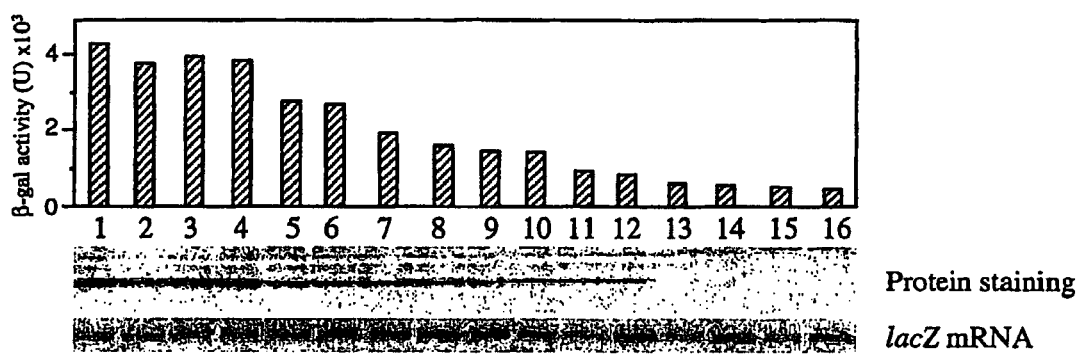
FIG. 7 is a combined bar graph and gel showing β-galactosidase activities, protein levels and lacZ mRNA levels of selected clones.

Enhanced Translation and not Transcription is Responsible for Higher β-Galactosidase Activity The clones obtained could be divided into four groups based on their β-galactosidase activities as clones with enzyme units in the range of (i) 43,000-35,000, (ii) 35,000-25,000, (iii) 25,000-10,000 and (iv) below 10,000. 16 clones representing all these four groups (4 from each) were selected and lacZ mRNA levels were checked in these clones using oligonucleotides corresponding to lacZ by primer extension (Etchegaray et al., 1999). FIG. 7 shows β-galactosidase activities, protein levels and lacZ mRNA levels in these clones. Similar to what was demonstrated in FIG. 6, the β-galactosidase activities corresponded to the protein levels. However, the clones showing high and low level of β-galactosidase activities showed similar levels of lacZ mRNA indicating that the higher β-galactosidase activities are not due to the transcription upregulation. Thus, the present inventors conclude that it is result of translational enhancement.

Figure 8:
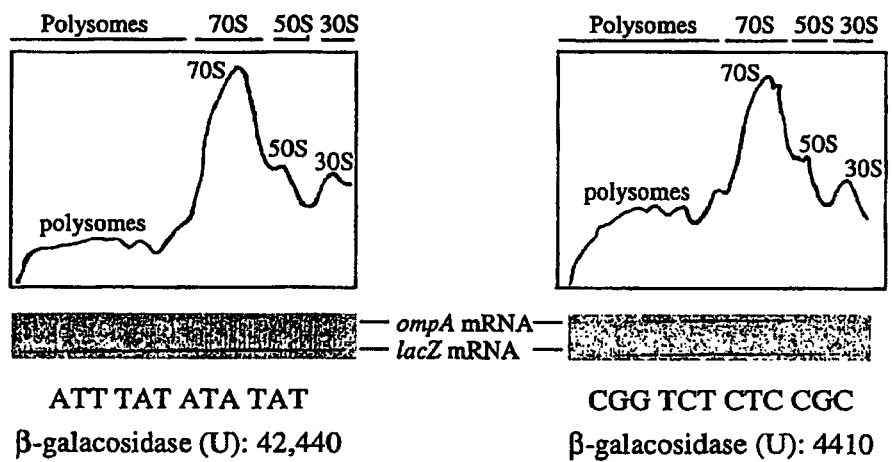
FIG. 8 are graphs and gels of the distribution of lacZ and ompA mRNA in polysome profiles of the clones showing highest and lowest β-galactosidase activities. Respective N$^{12}$ sequences (SEQ ID NO:14 and SEQ ID NO:26) are shown.

A/T (A/U)-Rich Element Downstream of the Initiation Codon Enhances Translation Initiation Next, the laboratory of the present inventors explored if translation initiation or elongation was responsible for this effect. Two clones showing the highest and lowest activity were chosen. Their sequences, SEQ ID NO:14 and SEQ ID NO:26, are shown in FIG. 8. The clone with β-galactosidase activity of 42,440 units had an A/T-rich sequence, ATT-TATATATAT (SEQ ID NO:14), downstream of the initiating codon, while the clone with activity of 4410 units had G/C-rich corresponding sequence, CGGTCTCTCCGC (SEQ ID NO:26). The ribosome profiles of these two clones were examined. The ribosomes were prepared and fractionated as described previously (Etchegaray et al., 1996 and Xia et al., 2001). The primer extension was carried out to examine distribution of the lacZ mRNA in the polysome and the 70S, 50S or 30S ribosomes. The ompA mRNA levels were also examined as a negative control. As seen from FIG. 8, the clone with higher activity showed higher ratio of lacZ to ompA mRNA in the polysome and the 70S fraction of the sucrose gradient as compared to the clone with lower β-galactosidase activity. This suggests that higher β-galactosidase expression is due to enhanced translation initiation, which is mediated by the A/T-rich sequence downstream to the initiation codon.

EXAMPLE 2

Identification of Translational cis Elements in the cspA mRNA Responsible for the LACE Effect The cspA mRNA contains a 159-base long 5'UTR (untranslated region), which is considered to play the most essential role in the LACE effect. The laboratory of the present inventors have demonstrated that the LACE effect is caused by trapping all cellular functional ribosomes by the cspA mRNA, thereby inhibiting all the other cellular mRNAs to form the initiation complexes for translation. This ability of the cspA mRNA to prevent all the other mRNAs from interacting with 30S ribosomes is speculated to be due to its highly efficient ability to form the initiation complex with ribosomes.

In prokaryotes, there are at least two important elements for translation initiation: one is the ribosome binding sequence, the so-called Shine-Dalgarano sequence (SD), and the other is the initiation codon AUG. In addition, a number of other elements for enhancing translation initiation have been reported (Gold et al., 1988). For example, it has been reported that there is an translation-enhancing element upstream of the SD sequence, termed "Epsilon" (Olins et al., 1989). It has been debated that there is also an element downstream of the initiation codon, called "downstream box" (Etchegaray et al., 1999a and 1999b; O'Connor et al. 1999). It is also important to note that the secondary structures in the 5'UTR are involved in the regulation of translation initiation. In particular the formation of a secondary structure at or near the SD sequence is often inhibitory for the formation of the initiation complex (Yamanaka et al., 1999).

The stability of bacterial mRNAs in the cells is another important factor in the regulation of expression of genes. Particularly, mRNAs such as the cspA mRNA having an unusually long 5'-UTR are in general more prone to endonuclease attack. Indeed, the cspA mRNA is highly unstable at higher temperature. At 37° C., its half-life is only less than 12 sec and this instability is shown to be attributed to the AU-rich sequence just upstream of the SD sequence. Base substitution mutations at this region has been shown to dramatically stabilize the cspA mRNA so that CspA production becomes constitutive at 37° C. (Fang et al., 1998). The elements in the cspA 5'-UTR essential for translation initiation enhancement will be identified. Through these analyses, it is possible to further improve the efficiency of translation initiation. The following approaches will be taken.

(i) Development of the System to Evaluate the Translation Initiation Efficiency

The LACE effect has been demonstrated to be caused by the highly effective translational initiation capacity of the cspA mRNA (Xia et al., 2001). The LACE effect is defined (a) by the antibiotic effect of a clone on colony formation of the cells carrying the clone at 15° C., (b) by the effect of the clone on the [$^{35}$S] methionine incorporation into total cellular proteins at 15° C., which can be analyzed by SDS-PAGE and (c) by growth curve of the cells carrying a LACE-causing clone.

In order to evaluate the strength of the LACE effect in individual clones, it is important for one to be able to quantitatively measure the LACE effect. For example, in case of pA01S, pA10S and pA30S constructed earlier by inserting a nonsense codon at 2nd, 11th, and 31st codons, respectively, in the cspA gene, the laboratory of the present inventors showed complete inhibition of colony formation at 15° C., and almost complete inhibitory effects on [$^{35}$S] methionine incorporation into cellular proteins at 15° C. after cold shock. However, these three clones may be able to be evaluated by their effectiveness of the LACE effect, if colony formation and protein synthesis are measured at higher temperatures. These clones carrying the stringent LACE effect may still retain their effective LACE effect at 20° C. or even at 25° C., while those carrying weaker LACE effect may start to form colonies at 20° C. and protein synthesis may be observed at this temperature. Therefore, a simple plating method should be able to evaluate the effectiveness of individual LACE-causing clones. The laboratory of the present inventors will test this method with the LACE-causing clones available in their laboratory, pA01S, pA10S, and pA30S (Xia et al., 2001). Cells harboring these plasmids will be plated on four LB agar plates and incubated separately at 37, 25, 20 and 15° C. The strength of the LACE effect will be classified by examining inhibition of colony formation at higher temperatures and also by the colony sizes at a given temperature.

The LACE effects at different temperatures will then be confirmed by [$^{35}$S] methionine incorporation and growth curves. It is likely that one can obtain a similar result for evaluation of the LACE effectiveness for individual clones constructed by any one of these methods. However, as plating is the simplest method among the three, this method will be used if it is proved to be as effective as the others.

(ii) Analysis of the 5'-UTR of the cspA mRNA

Figure 9:
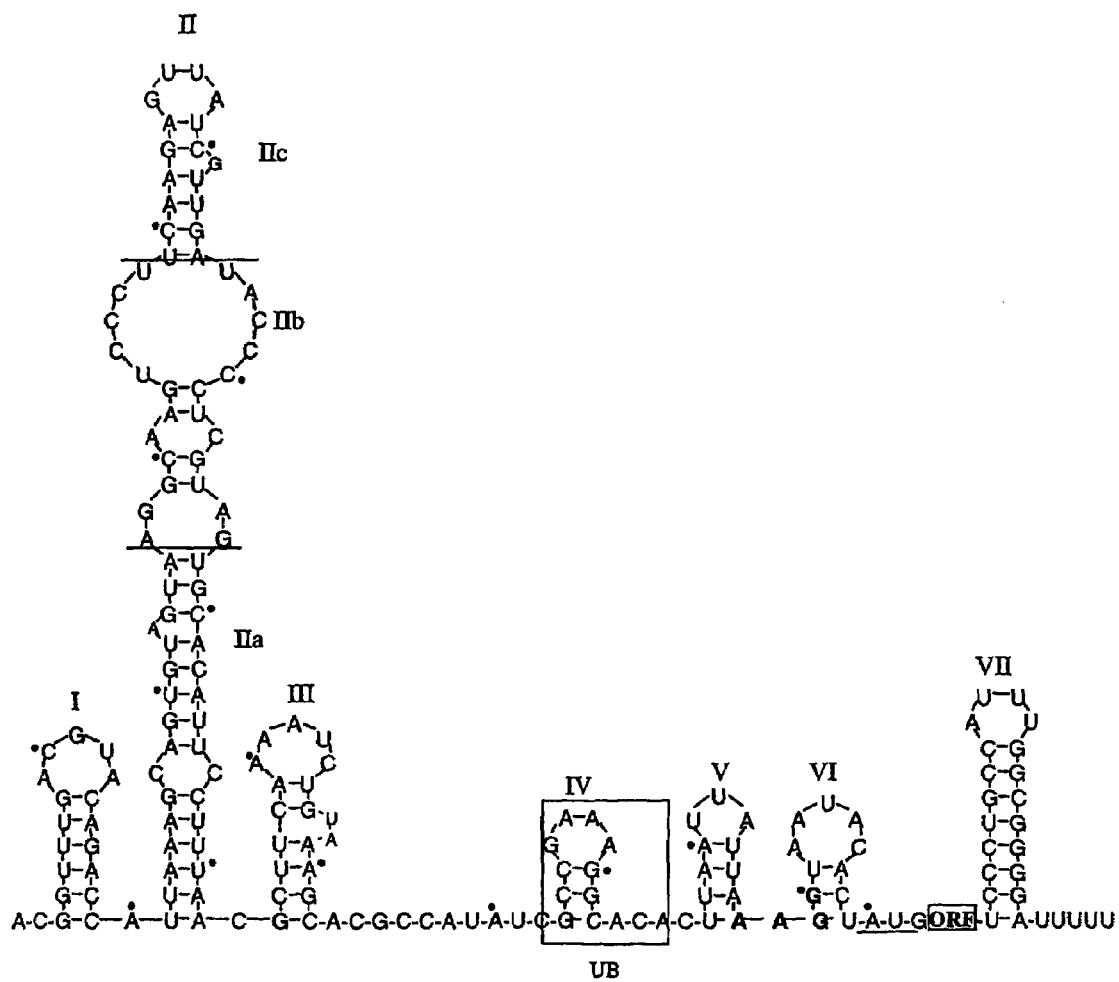
FIG. 9 shows a schematic representation of the structure of the cspA mRNA 5'-UTR. Every 10$^{th}$ base is dotted. The upstream box (UB) is boxed, the SD sequence is in bold, the initiating codon is underlined and the cspA ORF is indicated in bold and is boxed. The 5'-UTR sequence upstream of the cspA ORF corresponds to SEQ ID NO:48 and 3'-UTR sequence downstream of the cspA ORF corresponds to SEQ ID NO:49.

The secondary structures of a given RNA can be drawn in a number of different ways, and in particular, the exact secondary structures assumed by one mRNA in a cell are hard to be determined. Nevertheless, one can use a computer program to predict a likely, stable secondary structure of an mRNA. FIG. 9 shows the most stable secondary structure of the 5'-UTR of the cspA mRNA by computer analysis using the Zuker program (version 3.1 available at www.bioinfo.math.rpi.edu) for RNA folding. It shows that there are 6 secondary structures from I to VI and their stabilities are calculated to be −7.0, −14.8, −2.1, −8.3, 2.7, 1.5 Kcal, respectively. The secondary structure marked VII is the one formed at the 3' end and is considered to be β-independent transcription terminator.

Among the six secondary structures, structure I is known to be the Cold Box which is important for the stability of the cspA mRNA; hence, it cannot be eliminated. In the present approach to study the role of other structures from II and V, they will be deleted one by one to examine the effect of the deletion on the LACE effect using pA30S that has a nonsense codon at the 31st position in the coding sequence of cspA (Xia et al., 2001). If any effects by the deletion are found, in particular in the case of structure II, this large structure will be further dissected into small fragments. The stem region can be further divided into three parts, IIa, IIb and IIc as shown in FIG. 9. The following deletions will be constructed; ΔIIa, ΔIIb, ΔIIc, ΔIIbΔIIc, ΔIIaΔIIb, and ΔIIaΔIIc. These deletions in pA30S will be examined for their LACE effect using the plating method developed in section (i).

The Role of Structure IV

This region was earlier shown play an important role in translation efficiency (Yamanaka et al., 1999). The laboratory of the present inventors reported that a 13-base sequence named the upstream box (bases 123 to 135; UB sequence) which is highly conserved in cspA, cspB, cspG and cspI and is located 11 bases upstream of the SD sequence might be another cis element involved in translation efficiency of the cspA mRNA in addition to the SD sequence (Xia et al., 2001 and Yamanaka et al., 1999). The exact requirement of this structure will be examined by further dissecting the structure by deletion of smaller regions within the structure and by base substitutions.

The Role of Structure V

It is also interesting to note that there is a cis-element upstream of the SD sequence termed "Epsilon" that has been proposed to enhance translation of a gene in the Bacteriophage T7 (Olins et al. 1989). The Epsilon sequence, UUAACUUUA (SEQ ID NO:27), was originally found in the bacteriophage T7 gene 10 leader region. It has been reported that when the complementarity to 16S rRNA was extended, the epsilon was converted from an enhancer to an independent initiator of translation. It has been shown that Epsilon displayed maximal activity as a translational initiator at its natural 9-nucleotide-long complementarity to 16S rRNA and at a 16-nucleotide-long distance to the initiation codon. Under these conditions its efficiency was comparable with that of the consensus Shine-Dalgarno sequence (Golshani et al., 2000). The sequence of structure V is similar to Epsilon (FIGS. 9, 10A and 10B).

First, the 10-base sequence, UUAAUUAUUA (nucleotides 16-25 of SEQ ID NO:28), immediately upstream of the SD sequence (AAGG) will be analyzed for its role in the LACE effect. This Epsilon-like sequence consists of only A and U residues. Various deletion mutations (mutants 1, 2, 9, 10 and 11 in FIG. 10A) as well as substitution mutations will be constructed (mutants 3 to 8). The effects of these mutations on the LACE effect will reveal if there is a unique sequence requirement in this element as proposed for the Epsilon sequence. If the laboratory of the present inventors is able to demonstrate that the 10-base sequence has a significant role in enhancing translation (or LACE effect), the sequence will be examined for whether it can by itself be capable of initiating translation even without the SD sequence. For this purpose, the cspA SD sequence (AAGG) will be eliminated by mutating it to AACC (mutation 12 in FIG. 10B). If mutant 12 can exert the LACE effect, the 10-base sequence can be deleted to confirm that this region is indeed required for ribosome binding (mutant 13). Subsequently, the requirement of the distance between the Epsilon-like sequence and the initiation codon will be determined by deletion mutations as shown in mutants 14, 15 and 16.

It is possible that the so-called Epsilon sequence just functions because of its AU-richness without any sequence specificities. For this reason, the laboratory of the present inventors will also scramble or elongate the AU sequence from the present 10-bases to AU sequences 13-, 14- and 16-bases in length to examine their effect on the LACE effect. If the AU-rich sequence is indeed able to enhance translation, polysome patterns will be compared between the wild-type cspA RNA, mutant 1 (FIG. 10A) and mutant 12 (FIG. 10B) to confirm that the LACE effect is resulting from trapping cellular ribosomes.

Further confirmation of the role of structure V in translation enhancement will be carried out with pAlacZ that has been already constructed containing the cspA promoter, 5' UTR and the coding region of cspA up to its 13th codon fused to lacZ gene. Deletions and substitution mutations similar to the ones described above will also be created using this pAlacZ vector. The ΔcspA cells will be used as host for transformation to avoid the autoregulating effect of cspA produced from the chromosomal gene, and the level of cspA expressed from these plasmids will be examined by β-galactosidase assays. Through these experiments, the exact role of structure V in translation initiation will be determined.

EXAMPLE 3

Construction of the Cold-Shock Vectors

Figure 11B:
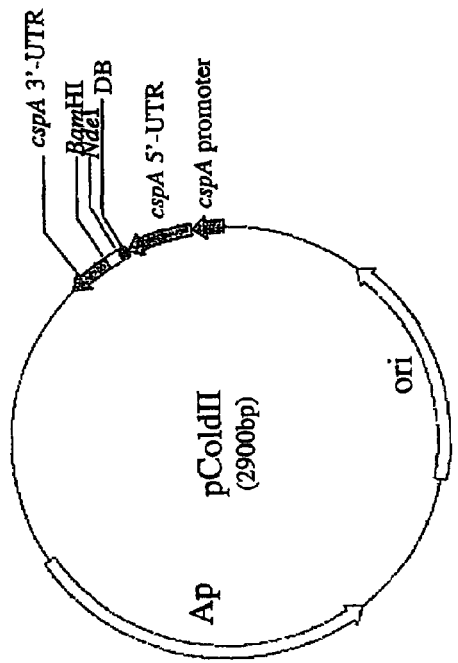
FIGS. 11A-11C show schematic representations of the structures of the pCold I, II and III vectors. The (His)$_6$ feature in FIG. 11A is identified herein by SEQ ID NO:52.
Figure 11C:
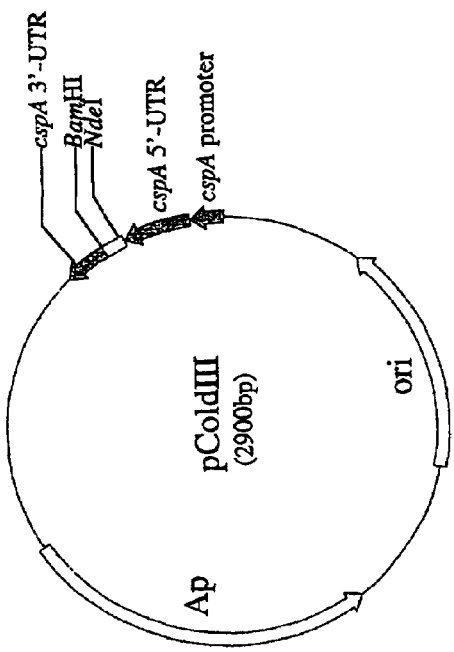
Figure 11A:
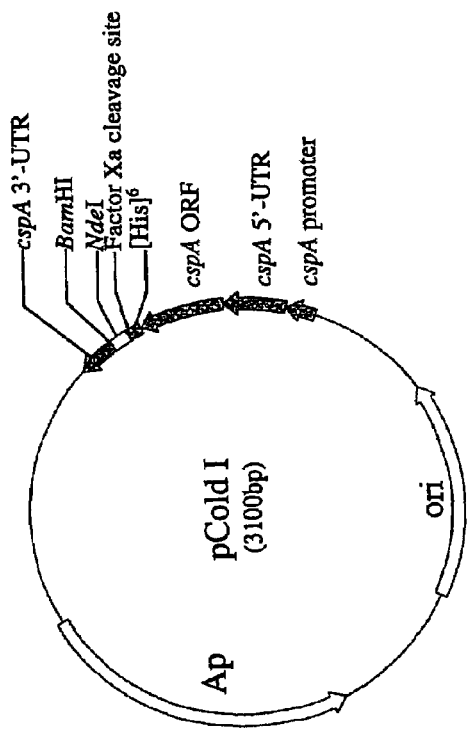

Cold-shock vectors in three forms will be constructed. In the first type, pColdI (FIG. 11A), is a vector in which the coding region of a gene is cloned as a fusion protein with the entire coding region of CspA. SEQ ID NO:45 as shown in FIG. 12A is present as an insert within the blunted HindIII-EcoRI sites of pUC19 (New England BioLabs, Beverly, Mass.). The second vector, pColdII (FIG. 11B), is a vector in which the coding region of a gene of interest is cloned after the 7th codon, where codons 1 to 7 are MetAsnHisLysVal-HisMet (SEQ ID NO:50) at a unique NdeI site created at the 7th Met codon. This extra sequence is encoded by the cis-translation enhancing element (ATGAATCACAAAGTG CATATG; SEQ ID NO:9, where the NdeI site is underlined) with which a cloned gene expression was shown to be 8-fold higher than a clone without this sequence (Etchegaray et al., 1999). SEQ ID NO:46 as shown in FIG. 12B is present as an insert within the blunted HindIII-EcoRI sites of pUC19. The third type, pColdIII (FIG. 11C), is a vector in which the coding region is cloned directly at the initiation codon using an NdeI site. In this vector, SEQ ID NO:47 as shown in FIG. 12C is present as an insert within the blunted HindIII-EcoRI sites of pUC19.

The three vectors, pColdI, pColdII, and pColdIII are identical vectors in that they all have a pUC19 background having the cspA promoter, the cspA 5'-UTR region and the cspA 3'end transcription terminator site. The difference being that in addition to this, pColdI has the coding region of cspA, while pColdII has the AT rich DB sequence. By including the coding region of cspA in pColdI, advantage is taken of its built-in high efficiency translation initiation property. It is also possible that the folding of the CspA domain at the N-terminal end may help the folding of the cloned gene product, as shown in the case of MBP (maltose-binding protein)-fusion proteins. In addition, pColdI is designed to have a six-His tag followed by the factor Xa cleavage site upstream of the NdeI cloning site in such a way that the product produced from this vector can be purified by a Ni-NTA column and that the N-terminal fragment can be removed by factor X cleavage.

It is important to note that when the pColdII vector is used, six amino acid residues, MetAsnHisLysValHis (residues 1-6 of SEQ ID NO:50) are added in front of the initiation codon of a given gene. Therefore, it has to be checked if this extra N-terminal extension affects the structure and function of a cloned gene product for each case. Advantage can be taken of this extra sequence to develop antisera against this sequence, which may be used for identification of the product and for purification if necessary.

All of these vectors are designed in such a way that a NdeI-BamHI fragment of a gene of interest can be cloned in the same reading frame and is mutually exchangeable between pCold and conventional pET vectors. In case a gene of interest is toxic for *E. coli* cell growth, where even a low level of leaky expression of the gene may cause a problem during growth at 37° C. For this reason, pColdI, pColdII and pColdIII having the lacI operator sequence, ATTGTGAGCG-GATAACAATTGATGTG (SEQ ID NO:10), immediately downstream of the cspA transcription initiation site will be constructed so that the expression of a cloned gene can be induced at low temperature only in the presence of IPTG. These pCold vectors will be termed pColdIo, pColdIIo and pColdIIIo, respectively.

In addition, an attempt will be made to determine the best possible SD sequence for higher cold-shock expression and the effect of the sequence downstream of the initiation codon (downstream box) as follows:

(i) The SD Sequence

The SD sequence found in the cspA mRNA (AAGG) is not the best SD sequence compared with a possible SD sequence which has the highest complementarity with the 3' end of 16S RNA. It may be improved by changing the cspA SD region to a longer consensus sequence, for example to AAGGAGGU by inserting AGG in the cspA mRNA. The SD sequence will be changed base by base by point mutations as shown in FIGS. 10A and 10B. Finally, the best SD sequence will be determined for the vector.

(ii) The Translation-Enhancing Effect by a Sequence Downstream of AUG in pColdIII The so-called Downstream Box (DB) effect indeed exerts its effect on translation initiation as judged from the experiments on the analysis of random sequences added at the regions from the 4th codon to the 7th codon (12 base sequences). As shown in Example 1 (FIG. 5), the DB sequences that significantly enhance the LACE effect basically consist of AT-rich sequences (but not the complementary sequence to 16S rRNA as originally proposed by Sprengart and his coworkers (1996). Interestingly, γ-interferon which is expressed at a very high level, even if it expressed directly from its own initiating codon (FIGS. 4A and 4B), has nine A/T residues out of twelve residues in this region. When the pColdIII vector is used, one can increase the AT content of the region from codon 4 to codon 7 replacing the third base of each codon to A or T it is G or C. This can be done without altering the amino acid sequence of this region because of degeneracy of the codon usage. Once a gene is cloned into pColdIII, whether or not the effect of the changed AT content in the first 7 codons is better for expression of the genes product of each clone will be examined.

EXAMPLE 4

Improvement of the Host System

In order to obtain the maximal yield of a protein to be expressed using the cold-shock vectors described above, the present inventors would like to improve the host system and to establish the growth conditions at low temperature. Important considerations for the host improvement are; (i) stabilization of the mRNA for the cloned gene, (ii) prolonging of the acclimation phase to block the cold-shock adaptation and (iii) increased production of cold-shock ribosomal factor such as CsdA, which may enhance the translation initiation and protein synthesis.

(i) Prolonged expression of cloned proteins at 15° C. Using pnp Deletion Cells as Host Cells Upon cold shock, *E. coli* cell growth transiently stops, and during this acclimation phase, specific-cold shock proteins are highly induced. At the end of the acclimation phase, their synthesis is reduced to new basal levels, while the non-cold-shock protein synthesis is resumed, resulting in cell growth reinitiation. Polynucleotide phosphorylase (PNPase) is a cold-shock-inducible exoribonuclease and a component of RNA degradosome involved in mRNA degradation. PNPase has been shown in the laboratory of the present inventors to be required to repress Csp production at the end of the acclimation phase. PNPase was found to be essential for selective degradation of csp mRNAs at 15° C. (Yamanaka et al., 2001). In a pnp mutant, the induction of Csps upon cold shock was normally observed as in the wild-type strain; however, their production was no longer autoregulated and was maintained at high levels throughout cold-shock treatment. This resulted in cells' growth arrest and a dramatic reduction of colony forming ability below 25° C. As a result, upon cold shock, cells maintained a high level of Csps even after 24 h. In a poly (A) polymerase mutant and a CsdA RNA helicase mutant, Csp expression upon cold shock was significantly prolonged, indicating that PNPase in concert with poly (A) polymerase and CsdA RNA helicase plays a critical role in cold-shock adaptation. Therefore, the use of the pnp deletion strain as a host for our cold-shock vectors is likely to help to maintain the cloned gene expression for a much longer time period. Such cells are already available in our laboratory. It is expected that in the absence of PNPase, cspA expression from the cold-shock vectors of the present invention will be prolonged, resulting in prolonged expression of the proteins of interest. The pnp deletion cells will be transformed with the cold-shock vectors containing the inserts corresponding to the genes encoding proteins of interest and the cells will be grown at 37° C. to the OD600 nm of 0.5 and then transferred to 15° C. Samples will be removed at 12 h intervals from 0-120 h to analyze the protein production by SDS-PAGE.

(ii) Prolonged Expression of Cloned Proteins at 15° C. Using rbfA Deletion Cells as Host Cells The gene rbfA encodes a 15 kDa protein (RbfA) that associates with free 30S but not 70S ribosomal subunits (Dammel et al., 1995). The gene was originally isolated as a multicopy suppressor of a dominant cold-sensitive mutation located in the 5' helix of 16S rRNA. The rbfA deletion mutant shows impaired growth at low temperature in a similar manner as in the pnp deletion cells (Dammel et al., 1995). The laboratory of the present inventors showed that RbfA is a cold-shock protein and in the rbfA deletion strain in spite of severe growth inhibition at low temperatures, cold-shock proteins and ribosomal proteins were highly induced and their expression became constitutive in a manner similar to that with the pnp deletion cells (Dammel et al., 1995). The laboratory of the present inventors have recently shown that RbfA has dual function in that it is involved in 30S ribosomal subunit maturation and translation initiation at low temperature. Considering the fact that deletion of rbfA results in constitutive expression of cold-shock proteins such as CspA, these cells will be ideal for expression of proteins using the cold-shock vectors at 15° C.

pnp and rbfA deletion strains have already been constructed and will double deletion mutants of these two genes will be created for expression of proteins using cold-shock vectors. The rbfA mutant strain, named BX41, was constructed by transducing a disrupted rbfA allele from strain CD28. CD28, disclosed in Dammel and Noller (1995), was obtained from their laboratory and transduced to MC4100 using P1 phage. The pnp mutant strain, disclosed in an article from Dr. Kushner's laboratory, Arraiano et al. (1988), was obtained from his laboratory.

Phage P1vir-mediated transduction (Miller, 1992) of the pnp strain with the rbfA strain will be used to create the double deletion mutant. For instance, a P1 phage is used to make rbfA mutant strain lysate, and then the rbfA, pnpase double mutant is made by P1 transduction using rbfA lysate and pnpase (pnp) mutant strain. The rbfA PCR product of each colony after P1 transduction is checked to confirm that they are rbfA mutants. Competent cells of these mutant strains are made and then transformed with the pINrbfA plasmid into the competent cell, incubated at 15° C. and checked for cold sensitivity to confirm the double mutation.

(iii) The Role of CsdA on the Cloned Gene Expression

Poly (A) polymerase of *E. coli* was reported to interact with RNA, RNase E and DEAD-box RNA helicases of RhlE, SrmB and CsdA by means of Far Western analysis (Raynal et al., 1999). Among them CsdA is a cold shock-inducible protein and has an activity to unwind double-stranded RNA in the absence of ATP (Jones et al., 1996). Similar to RbfA, CsdA is essential for growth at low temperature (data not shown). CsdA function was proposed to be essential for ribosome function to increase translational efficiencies of mRNAs by unwinding stable secondary structures formed at low temperature (Jones et al., 1996).

A csdA deletion mutant, in which cold-shock gene expression is prolonged similar to that in pnp and rbfA deletion strains, was constructed. The kanamycin resistance gene (1.3K HincII fragment) from pUC7 Km(Pst) was inserted into the middle of the coding region of the csdA gene (alternatively deadD and mssB) at the EcoRV site in pKX164, yielding pKNJ9026. The linearized pKNJ9026 DNA fragment containing the disrupted csdA (csdA::Kan) was then introduced into the chromosome of a recD mutant FS1576. Kanamycin-resistant transformants were isolated and the disruption of csdA on the chromosome was confirmed by Southern hybridization. The csdA::Kan mutation was transduced into the wild-type strain MC4100, yielding KNJ130. However, the csdA deletion may not assist the expression of a cloned gene as predicted in the case of pnp and rbfA deletions. This is because CsdA may be required for unwinding of mRNAs for non-cold-shock proteins. As our cold-shock-vector system will be used for non-cold-shock proteins, CsdA in the host system may even help the expression of the cloned gene. Note that in contrast to CsdA, RbfA is likely not to be required for the cloned gene expression with our cold-shock vectors as the elements required for translation initiation are from cspA.

On the basis of these considerations, the effects of not only csdA deletion but also CsdA overexpression on the expression of a number of genes cloned in our vector will be examined. The overexpression of CsdA will be carried out by cloning these genes in a pINIII vector (Inouye, 1983) and will be cotransformed in the cells with the cold-shock vectors. Using pINIII vector, CsdA can be induced with IPTG before cold-shock, and its effect on the cold-shock induction of the expression of the gene of interest can be evaluated.

(iv) Standardization of Growth Medium Conditions

The goal of this study is to synthesize a protein of interest at a level of 90-95% of total cellular protein synthesis with a protein yield of higher than 60-70% of the total cellular proteins. Thus cell lysates after removal of insoluble materials such as the membrane fraction and the ribosomal fraction by centrifugation may be used for NMR spectroscopy without any further purification. In such cases, even whole cell suspensions without lysis could be applied for NMR spectroscopy. Therefore, by exchanging the medium after cold shock (for example from a $^{12}$C-glucose/$^{14}$NH$_4$Cl-base medium to a $^{13}$C-glucose/$^{15}$NH$_4$Cl-base medium), only the protein of interest can be labeled with isotopes, eliminating the purification process. Assuming that a protein of a molecular weight of 20 kDa is produced at a level of 60% of the total cellular protein (note that only this protein is newly synthesized upon cold shock), the total yield of the protein per liter is expected to be approximately 120 mg. If this protein is produced in a soluble form and the cell lysate is prepared in 4 ml from the culture (sonicated and subsequently ultracentrifuged to remove cells debris, the membrane fraction and the ribosomal fraction) one can obtain 30 mg/ml or 1.5 no solution of the protein of interest, which can be directly used for NMR spectroscopy. As NMR spectroscopy can be done with less than 1 ml, the culture size now can be reduced to 250 ml, which cuts the usage of expensive $^{13}$C-glucose and $^{15}$N—NH$_4$Cl [or ($^{15}$NH$_4$)$_2$SO$_4$] to a quarter. Amino acids labeled with $^{15}$N, $^{13}$C or both can be used singly or in combination. Furthermore, as the cells are unable to grow upon cold shock under the proposed conditions, the overall carbon utilization should be much less than that of the growing cells. Therefore, the concentration of glucose in the medium could be less than the concentration usually used for $^{13}$C-glucose (0.2%). This further saves the consumption of the expensive $^{13}$C-glucose.

In order to determine how much glucose is converted during cold-shock incubation of cells affected by the LACE effect, the effect of glucose concentrations (0.2%, 0.15%, 0.1%, 0.05% and 0.025%) on the protein production after cold shock will be tested. Cells harboring the expression system described Example 1 will be tested. Before cold-shock, cells (10 ml cultures) will be collected by centrifugation, washed with M9 medium, and resuspended in 10 ml of M9 medium containing different concentrations of glucose. These cultures together with a control culture (no centrifugation; a total of 6 cultures) will be incubated at 15° C. and the protein production will be examined every 24 h for 5 days. In this fashion, the minimum requirement of glucose in the medium will be determined without reducing the protein yield. After determining the glucose concentration, that condition will be applied for the few clones available, which produce soluble proteins in a high yield to label them with $^{13}$C and $^{15}$N. NMR spectroscopy on these proteins using cell lysate will be carried out and the effectiveness of the cold-shock vectors will be evaluated.

EXAMPLE 5

NMR Spectroscopy without Protein Purification

NMR spectroscopy analysis [$^1$H-$^{15}$N)HSQC] was performed using supernatant from whole cell lysate without protein purification. For this experiment, the ATP-binding domain of EnvZ (164 residues), an osmosensing histidine kinase in *E. coli* was used as a model system because its NMR solution structure has already been resolved in a collaboration between the laboratory of the present inventors and Dr. Ikura of the Ontario Cancer Institute (Nature 386:88-92, 1998).

A 500 ml culture of *E. coli* BL-1 harboring pCold-EnvZ (ATP-binding domain or fragment B) in M9 minimal medium was grown to OD$_{600nm}$ of 0.6. Cells were collected by centrifugation and resuspended in 250 ml prechilled M9 minimal medium containing 0.1% $^{15}$NH$_4$Cl and 0.4% glucose. After the resuspended cells were grown for 48 hrs in 15° C., the cells were harvested by centrifugation and lysed by repeated freeze-thaw and sonication. After separating the cell debris and the membrane fraction (pellet) by ultracentrifugation, the resultant supernatant was directly used for NMR analysis.

Figure 14A:
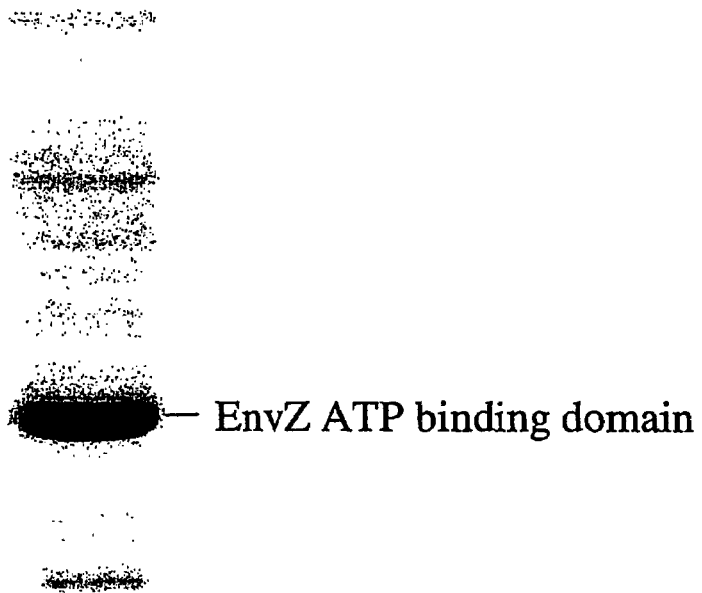
FIGS. 14A and 14B show a SDS-PAGE gel stained with Coomassie Brilliant Blue of the supernatant (500 ml culture of E. coli BL21 harboring pColdI-EnvZ ATP binding domain incubated for 48 hrs. cold shock) after ultra centrifugation stained with Coomassie Brillant Blue (FIG. 14A) and a SDS-PAGE gel of total cell lysate, pellet and supernatant following cold shock (FIG. 14B) of E. coli BL91. EnvZ ATP-binding domain is also known as fragment B.
Figure 14B:
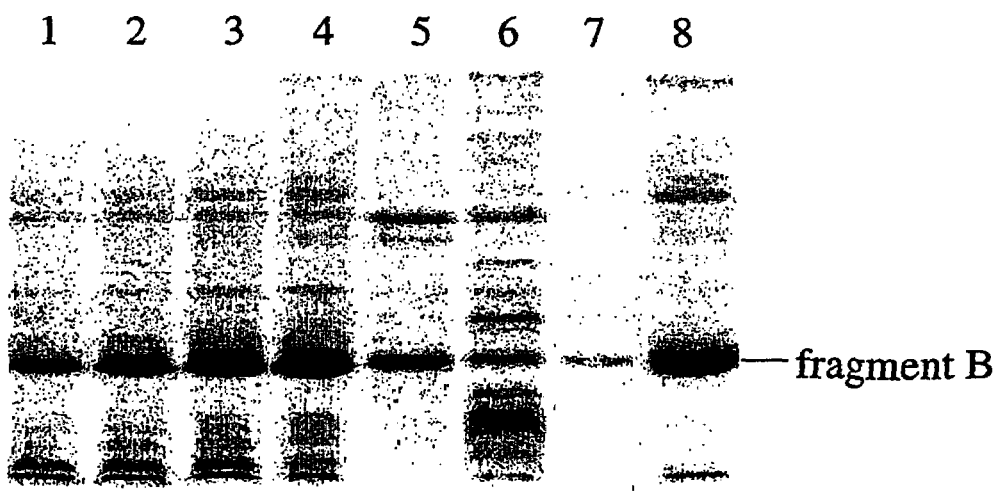

FIG. 14A shows a SDS-PAGE gel of the resultant supernatant after ultracentrifugation stained with Coomassie Brilliant Blue. The EnvZ ATP-binding domain in FIG. 14A represents almost 80% of the total protein sample. Of particular note, most of the minor bands seen in the gel in FIG. 14A are those proteins carried over from the cells at 37° C., and therefore, are not labeled with $^{15}$N. FIG. 14B shows an SDS-PAGE gel of total cell lysate, and the resultant pellet and supernatant after ultracentrifugation.

Figure 15A:
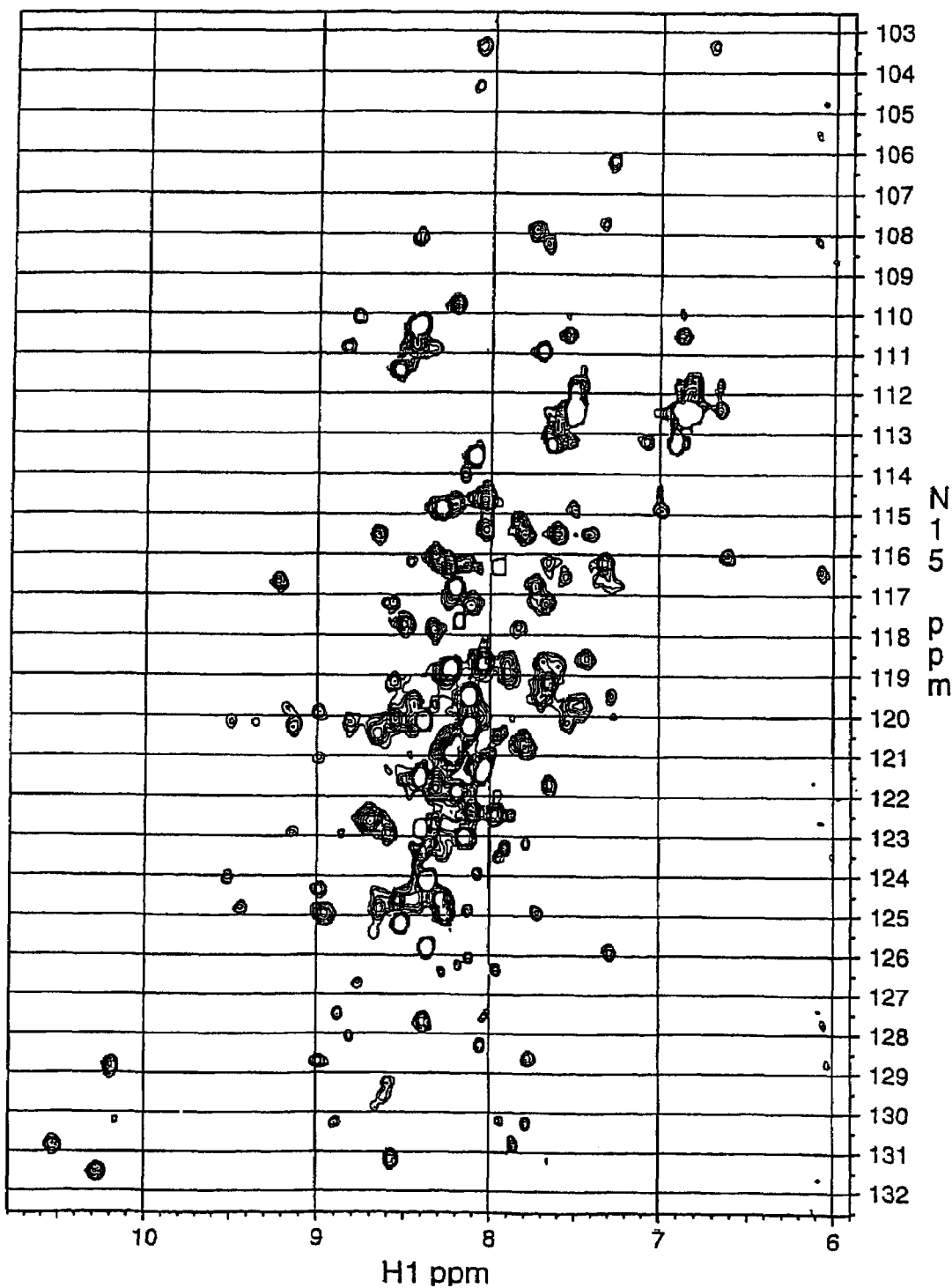
FIGS. 15A and 15B show the ($^1$H-$^{15}$N) HSQC NMR spectrum of cell lysate supernatant containing EnvZ ATP-binding domain without purification (FIG. 15A) and the HSQC NMR spectrum of purified EnvZ ATP-binding domain (FIG. 15B).
Figure 15B:
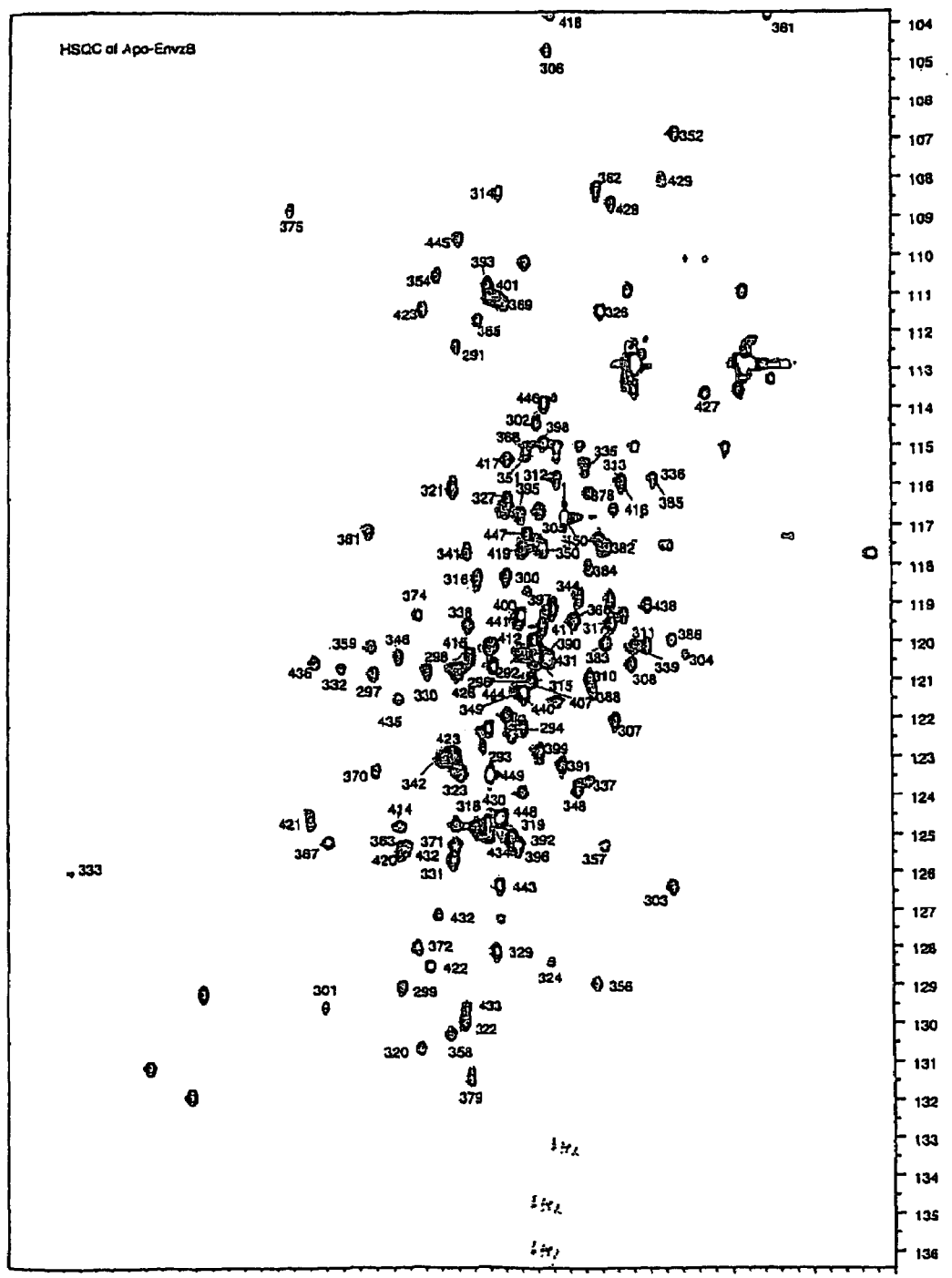

A distinct ($^1$H-$^{15}$N) HSQC NMR spectrum, comparable to the spectrum of purified EnvZ ATP-binding domain (FIG. 15B) was obtained from the supernatant of total cell lysate without any protein purification procedures (FIG. 15A). This approach of using the cold shock vector system to achieve exclusive labeling of a single membrane protein with $^{15}$N and/or $^{13}$C allows determination of the structure of heterologous proteins and membrane proteins in situ without protein purification.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Bae, W., P. G. Jones, and M. Inouye. 1997. CspA, the major cold shock protein of *Escherichia coli*, negatively regulates its own gene expression. J Bacteriol 179:7081-8.

Bae, W., B. Xia, M. Inouye, and K. Severinov. 2000. *Escherichia coli* CspA-family RNA chaperones are transcription antiterminators. Proc Natl Acad Sci USA 97:7784-9.

Brandi, A., R. Spurio, C. O. Gualerzi, and C. L. Pon. 1999. Massive presence of the *Escherichia coli* 'major cold-shock protein' CspA under non-stress conditions. Embo J 18:1653-9.

Dammel, C. S., and H. F. Noller. 1995. Suppression of a cold-sensitive mutation in 16S rRNA by overexpression of a novel ribosome-binding factor, RbfA. Genes Dev 9:626-37.

Etchegaray, J. P., and M. Inouye. 1999. CspA, CspB, and CspG, major cold shock proteins of *Escherichia coli*, are induced at low temperature under conditions that completely block protein synthesis. J Bacteriol 181:1827-30.

Etchegaray, J. P., and M. Inouye. 1999. A sequence downstream of the initiation codon is essential for cold shock induction of cspB of *Escherichia coli*. J Bacteriol 181:5852-4.

Etchegaray, J. P., and M. Inouye. 1999. Translational enhancement by an element downstream of the initiation codon in *Escherichia coli*. J Biol Chem 274:10079-85.

Etchegaray, J. P., P. G. Jones, and M. Inouye. 1996. Differential thermoregulation of two highly homologous cold-shock genes, cspA and cspB, of *Escherichia coli*. Genes Cells 1:171-8.

Fang, L., Y. Hou, and M. Inouye. 1998. Role of the cold-box region in the 5' untranslated region of the cspA mRNA in its transient expression at low temperature in *Escherichia coli*. J Bacteriol 180:90-5.

Fang, L., W. Jiang, W. Bae, and M. Inouye. 1997. Promoter-independent cold-shock induction of cspA and its derepression at 37 degrees C. by mRNA stabilization. Mol Microbiol 23:355-64.

Gold, L. 1988. Posttranscriptional regulatory mechanisms in *Escherichia coli*. Annu Rev Biochem 57:199-233.

Goldenberg, D., I. Azar, A. B. Oppenheim, A. Brandi, C. L. Pon, and C. O. Gualerzi. 1997. Role of *Escherichia coli* cspA promoter sequences and adaptation of translational apparatus in the cold shock response. Mol Gen Genet 256:282-90.

Golshani, A., V. Kolev, M. G. AbouHaidar, and I. G. Ivanov. 2000. Epsilon as an initiator of translation of CAT mRNA in *Escherichia coli*. Biochem Biophys Res Commun 273:528-31.

Inouye, M. 1983. Multipurpose expression cloning vehicles in *Escherichia coli*. New York Academic Press, NY.

Jiang, W., L. Fang, and M. Inouye. 1996. Complete growth inhibition of *Escherichia coli* by ribosome trapping with truncated cspA mRNA at low temperature. Genes Cells 1:965-76.

Jiang, W., L. Fang, and M. Inouye. 1996. The role of the 5'-end untranslated region of the mRNA for CspA, the major cold-shock protein of *Escherichia coli*, in cold-shock adaptation. J Bacteriol 178:4919-25.

Jiang, W., Y. Hou, and M. Inouye. 1997. CspA, the major cold-shock protein of *Escherichia coli*, is an RNA chaperone. J Biol Chem 272:196-202.

Jones, P. G., M. Mitta, Y. Kim, W. Jiang, and M. Inouye. 1996. Cold shock induces a major ribosomal-associated protein that unwinds double-stranded RNA in *Escherichia coli*. Proc Natl Acad Sci USA 93:76-80.

Jones, P. G., R. A. VanBogelen, and F. C. Neidhardt. 1987. Induction of proteins in response to low temperature in *Escherichia coli*. J Bacteriol 169:2092-5.

Kumar, A., R. A. Malloch, N. Fujita, D. A. Smillie, A. Ishihama, and R. S. Hayward. 1993. The minus 35-recognition region of *Escherichia coli* sigma 70 is inessential for initiation of transcription at an "extended minus 10" promoter. J Mol Biol 232:406-18.

Kushner et al., Stabilization of discrete mRNA breakdown products in ams pnp rnb multiple mutants of *Escherichia coli* K-12, J. Bacteriol. 170:4625-4633 (1988)

Miller, J. H. 1992. A Short Course in Bacterial Genetics: A Laboratory Manual and Handbook for *Escherichia coli* and Related Bacteria. Cold Spring Harbor Laboratory, Cold Spring Harbor, N.Y.

Mitta, M., L. Fang, and M. Inouye. 1997. Deletion analysis of cspA of *Escherichia coli*: requirement of the AT-rich UP element for cspA transcription and the downstream box in the coding region for its cold shock induction. Mol Microbiol 26:321-35.

Mujacic, M., K. W. Cooper, and F. Baneyx. 1999. Cold-inducible cloning vectors for low-temperature protein expression in *Escherichia coli*: application to the production of a toxic and proteolytically sensitive fusion protein. Gene 238:325-32.

O'Connor, M., T. Asai, C. L. Squires, and A. E. Dahlberg. 1999. Enhancement of translation by the downstream box does not involve base pairing of mRNA with the penultimate stem sequence of 16S rRNA. Proc Natl Acad Sci USA 96:8973-8.

Olins, P. O., and S. H. Rangwala. 1989. A novel sequence element derived from bacteriophage T7 mRNA acts as an enhancer of translation of the lacZ gene in *Escherichia coli*. J Biol Chem 264:16973-6.

Phadtare, S., J. Alsina, and M. Inouye. 1999. Cold-shock response and cold-shock proteins. Curr Opin Microbiol 2:175-80.

Phadtare, S., and Inouye, M. 2002. Cold Shock in "Encyclopedia of Environmental Microbiology". John Wiley & Sons, New York.

Phadtare, S., Yamanaka, K, and Inouye, M. 2000. The Cold Shock Response in The Bacterial Stress Responses. ASM-Press, Washington D.C.

Phadtare, S. U., M. Inouye, and K. Severinov. 2001. The nucleic acid melting activity of *Escherichia coli* CspE is critical for transcription antitermination and cold-acclimation of cells. J Biol Chem 276.

Raynal, L. C., and A. J. Carpousis. 1999. Poly(A) polymerase I of *Escherichia coli*: characterization of the catalytic domain, an RNA binding site and regions for the interaction with proteins involved in mRNA degradation. Mol Microbiol 32:765-75.

Sprengart, M. L., E. Fuchs, and A. G. Porter. 1996. The downstream box: an efficient and independent translation initiation signal in *Escherichia coli*. Embo J 15:665-74.

Vasina, J. A., and F. Baneyx. 1997. Expression of aggregation-prone recombinant proteins at low temperatures: a comparative study of the *Escherichia coli* cspA and tac promoter systems. Protein Expr Purif 9:211-8.

Vasina, J. A., and F. Baneyx. 1996. Recombinant protein expression at low temperatures under the transcriptional control of the major *Escherichia coli* cold shock promoter cspA. Appl Environ Microbiol 62:1444-7.

Wang, N., R. Yamanaka, and M. Inouye. 1999. CspI, the ninth member of the CspA family of *Escherichia coli*, is induced upon cold shock. J Bacteriol 181:1603-9.

Xia, B., J. P. Etchegaray, and M. Inouye. 2001. Nonsense mutations in cspA cause ribosome trapping leading to complete growth inhibition and cell death at low temperature in *Escherichia coli*. J Biol Chem 276:35581-8.

Xia, B., H. Ke, and M. Inouye. 2001. Acquirement of cold sensitivity by quadruple deletion of the cspA family and its suppression by PNPase Si domain in *Escherichia coli*. Mol Microbiol 40:179-88.

Xia, B., H. Ke, W. Jiang, and M. Inouye. 2001. The Cold Box stem-loop proximal to the 5'-end of the *Escherichia coli* cspA gene stabilizes its mRNA at low temperature. J Biol. Chem.

Yamanaka, K., L. Fang, and M. Inouye. 1998. The CspA family in *Escherichia coli*: multiple gene duplication for stress adaptation. Mol Microbiol 27:247-55.

Yamanaka, K., and M. Inouye. 2001. Induction of CspA, an *E. coli* major cold-shock protein, upon nutritional upshift at 37 degrees C. Genes Cells 6:279-90.

Yamanaka, K., and M. Inouye. 2001. Selective mRNA degradation by polynucleotide phosphorylase in cold shock adaptation in *Escherichia coli*. J Bacteriol 183:2808-16.

Yamanaka, K., M. Mitta, and M. Inouye. 1999. Mutation analysis of the 5' untranslated region of the cold shock cspA mRNA of *Escherichia coli*. J Bacteriol 181:6284-91.

---

What is claimed is:

1. A self-replicating vector which expresses a heterologous polypeptide, comprising:
   a cold shock inducible promoter and 5'-untranslated region (5'-UTR),
   wherein said vector comprises the nucleotide sequence of SEQ ID NO:45 or SEQ ID NO: 46.

2. A self-replicating vector which expresses a heterologous polypeptide, comprising a cold shock inducible promoter, 5'-UTR, and a lacI operator sequence immediately downstream of the transcription initiation site, wherein said vector comprises said lacI operator sequence inserted into the nucleotide sequence of SEQ ID NO:45 or SEQ ID NO:46.

3. The self-replicating vector of claim 2, wherein the lacI operator sequence is the nucleotide sequence of SEQ ID NO:10.

4. A prokaryotic host cell transformed with the self-replicating vector of claim 1.

5. The host cell of claim 4, which is *Escherichia coli*.

6. The host cell of claim 4, which is a polynucleotide phosphorylase mutant lacking polynucleotide phosphorylase activity.

7. The host cell of claim 4, which is a rbfA mutant lacking the 15 kDa RbfA protein that associates with free 30S ribosomal subunit but not the 70S ribosomal subunit.

8. The host cell of claim 4, which is a csdA RNA helicase mutant lacking csdA RNA helicase activity.

9. The host cell of claim 4, which is co-transformed with a vector which overexpresses csdA RNA helicase in said host cell.

10. A method for producing a heterologous polypeptide, comprising:
    inserting a nucleotide sequence encoding a heterologous polypeptide into the self-replicating vector of claim 1 or claim 2, wherein the nucleotide sequence encoding the heterologous polypeptide is operably linked to the cold shock inducible promoter and 5'-UTR;
    transforming a prokaryotic host cell with the self-replicating vector comprising the sequence encoding a heterologous polypeptide;
    culturing the transformed prokaryotic host cell in a nutrient medium at the normal physiological growth temperature of the host cell;
    subjecting the cultured host cell to cold shock by lowering the incubation temperature to a temperature at least 13° C. below the normal physiological growth temperature of the host cell to induce production of the heterologous polypeptide; and
    incubating the cold shocked host cell at the lowered incubation temperature to produce the heterologous polypeptide.

11. The method of claim 10, further comprising the step of recovering the produced heterologous polypeptide.

12. The method of claim 10, wherein the incubation temperature is lowered to at least 20° C. below the normal physiological growth temperature of the host cell.

13. The method of claim 10, further comprising the step of exchanging the nutrient medium with a medium containing a compound for detectably labeling the heterologous polypeptide after subjecting the cultured host cell to cold shock.

14. The method of claim 13, wherein said compound contains an isotope normally found in negligible amounts in the host cell.

15. The method of claim 14, wherein said isotope is $^{15}$N or $^{13}$C.

16. The method of claim 14, wherein said compound is selected from the group consisting of $^{15}$NH$_4$Cl, ($^{15}$NH$_4$)$_2$SO4, $^{13}$C-glucose, amino acid residues labeled with $^{15}$N, amino acid residues labeled with $^{13}$C, and amino acid residues labeled with both $^{15}$N and $^{13}$C.

17. The method of claim 14, wherein the host cell is a mutant lacking one or more of the major cold shock proteins.

18. The method of claim 17, wherein said mutant host cell lacks CspA.

19. The method of claim 17, wherein said mutant host cell lacks CspA, CspB, CspG, and CspE.

20. A method for obtaining a NMR spectrum of a heterologous polypeptide, comprising:
    isolating the cold shocked host cell incubated in the method of claim 13 at the lowered incubation temperature to produce the heterologous polypeptide detectably labeled with said compound; and
    conducting either whole cell NMR spectroscopy on the isolated cold shocked host cell or NMR spectroscopy on supernatant from cell lysate of the isolated cold shocked host cell to obtain a NMR spectrum of the heterologous polypeptide.

21. The method of claim 20, wherein whole cell NMR spectroscopy on the isolated cold shocked whole cell is conducted.

22. The method claim 20, wherein NMR spectroscopy on supernatant from cell lysate of the isolated cold shocked host cell is conducted.

* * * * *